(12) United States Patent
Xie

(10) Patent No.: US 9,186,156 B2
(45) Date of Patent: Nov. 17, 2015

(54) SURGICAL DRILL WITH DRIVE SHAFT AND DRILL BIT THAT, AFTER DISENGAGING THE DRILL BIT FROM THE DRIVE SHAFT, ALLOWS THE DRILL BIT TO BE DRIVEN IN REVERSE

(71) Applicant: Stryker Corporation, Kalamazoo, MI (US)

(72) Inventor: Mark Mingjun Xie, Comstock Township, MI (US)

(73) Assignee: Stryker Corporation, Kalamazoo, MI (US)

( * ) Notice: Subject to any disclaimer, the term of this patent is extended or adjusted under 35 U.S.C. 154(b) by 189 days.

(21) Appl. No.: 13/798,866

(22) Filed: Mar. 13, 2013

(65) Prior Publication Data

US 2013/0245629 A1    Sep. 19, 2013

Related U.S. Application Data

(60) Provisional application No. 61/610,779, filed on Mar. 14, 2012.

(51) Int. Cl.
  *A61B 17/00*    (2006.01)
  *A61B 17/16*    (2006.01)

(52) U.S. Cl.
  CPC ........... *A61B 17/162* (2013.01); *A61B 17/1622* (2013.01); *A61B 17/1624* (2013.01)

(58) Field of Classification Search
  CPC .................... A61B 17/1622; A61B 17/1624
  USPC .......................................... 408/139, 140, 142
  See application file for complete search history.

(56) References Cited

U.S. PATENT DOCUMENTS

| | | | | |
|---|---|---|---|---|
| 4,122,928 | A * | 10/1978 | Smith | 192/56.56 |
| 4,565,109 | A * | 1/1986 | Tsay | 475/305 |
| 4,832,542 | A * | 5/1989 | Johnson et al. | 408/139 |
| 5,071,293 | A | 12/1991 | Wells | |
| 6,665,948 | B1 | 12/2003 | Kozin et al. | |
| 2009/0024129 | A1 | 1/2009 | Gordon et al. | |
| 2011/0245833 | A1 | 10/2011 | Anderson | |
| 2015/0066030 | A1 | 3/2015 | McGinley et al. | |

* cited by examiner

*Primary Examiner* — Nicholas Woodall

(57) ABSTRACT

A chuck assembly for use with a surgical drill. The chuck assembly is configured to receive a drill bit. The chuck assembly includes an input drive shaft and a linear clutch coupled to the input drive shaft. The linear clutch has an inner coupler. The linear clutch transfers rotary motion from the input drive shaft to the inner coupler when the inner coupler is exposed to a displacing force that causes the inner coupler into engagement with the input drive shaft. A rotary clutch is coupled to the input drive shaft. The rotary clutch has an outer coupler. The rotary clutch transfers rotary motion from the input drive shaft to the outer coupler only when the input drive shaft rotates in a reverse direction.

20 Claims, 32 Drawing Sheets

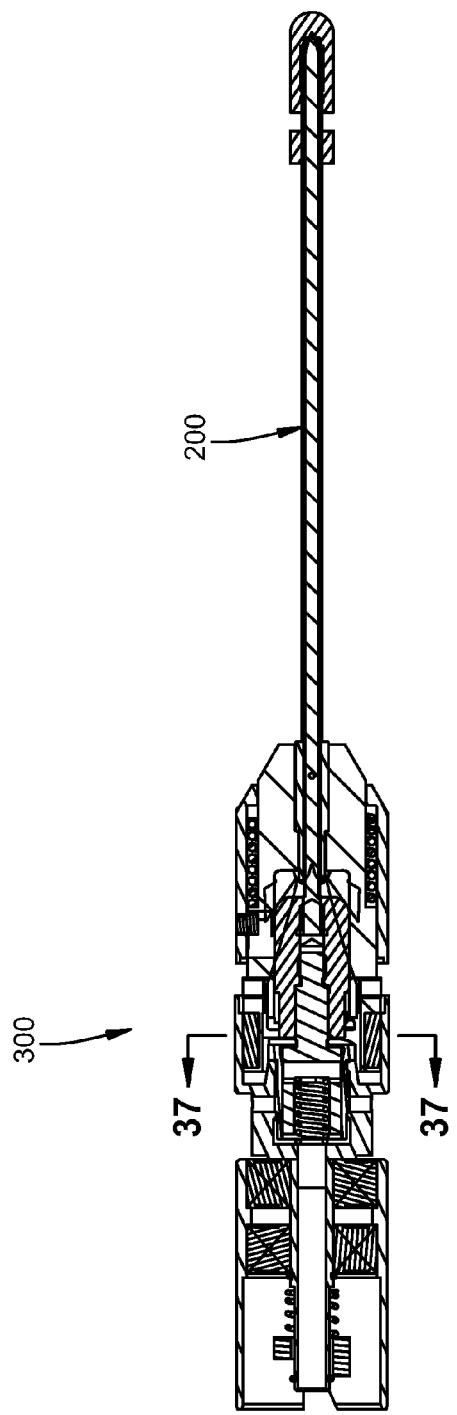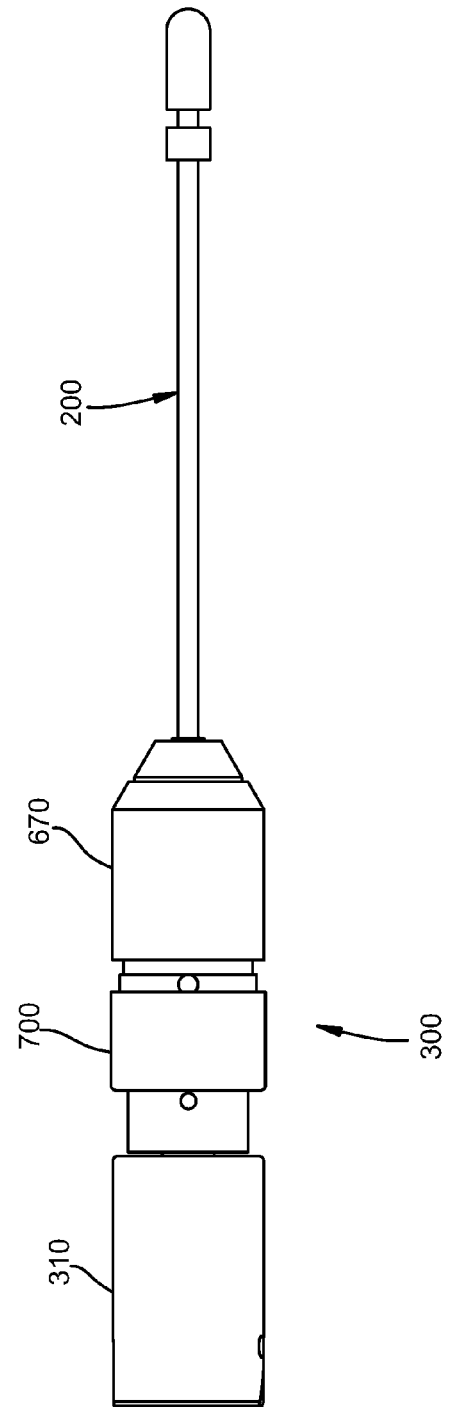

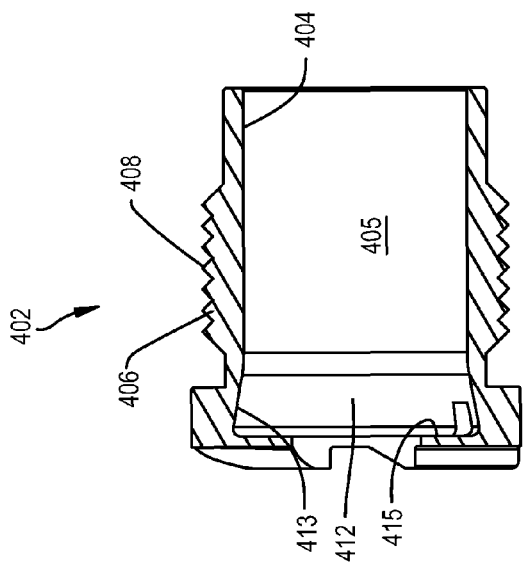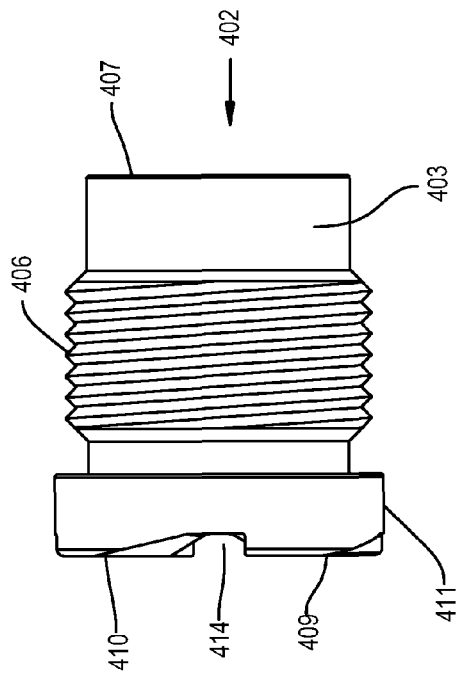

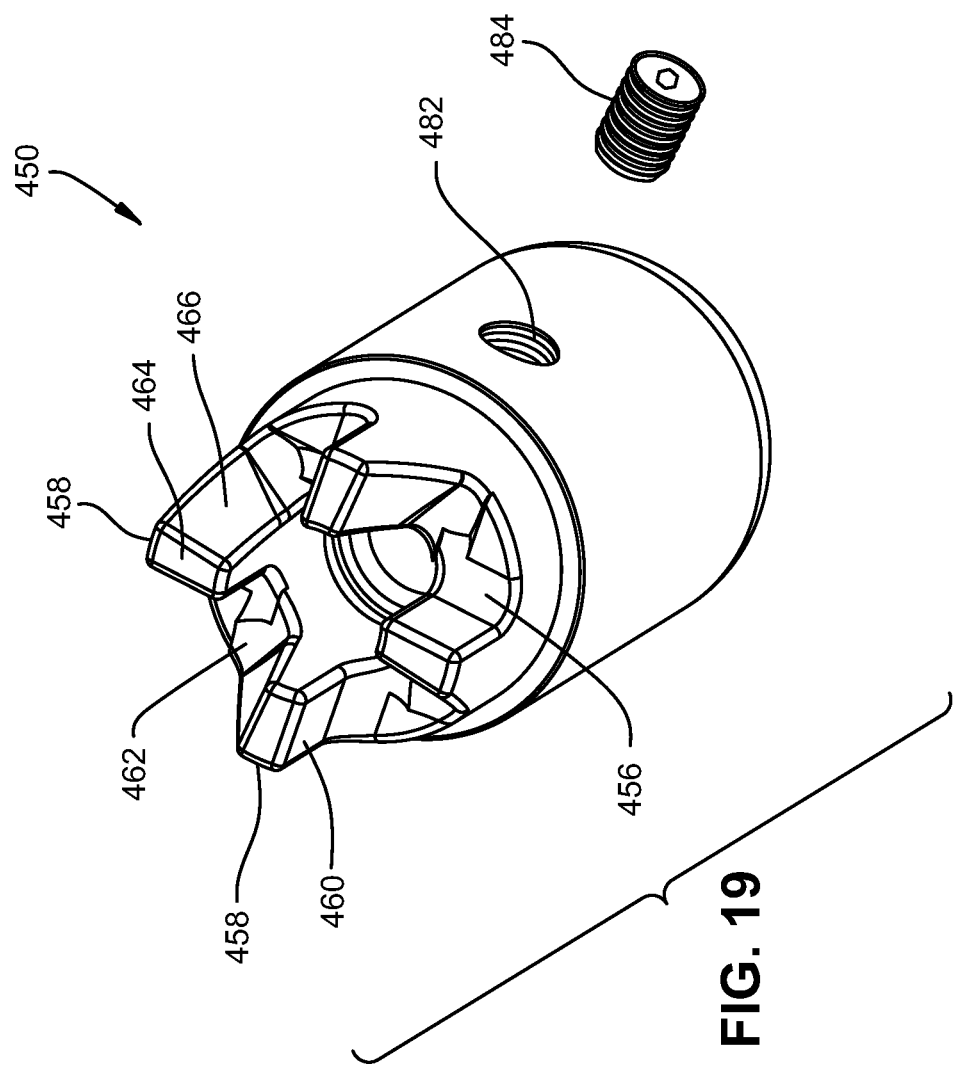

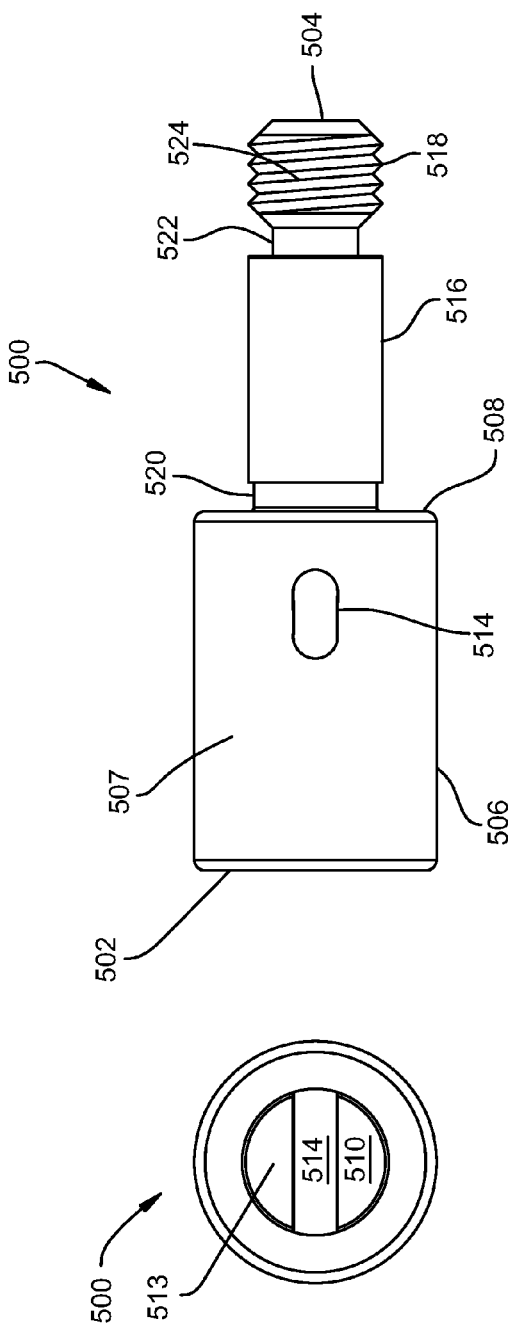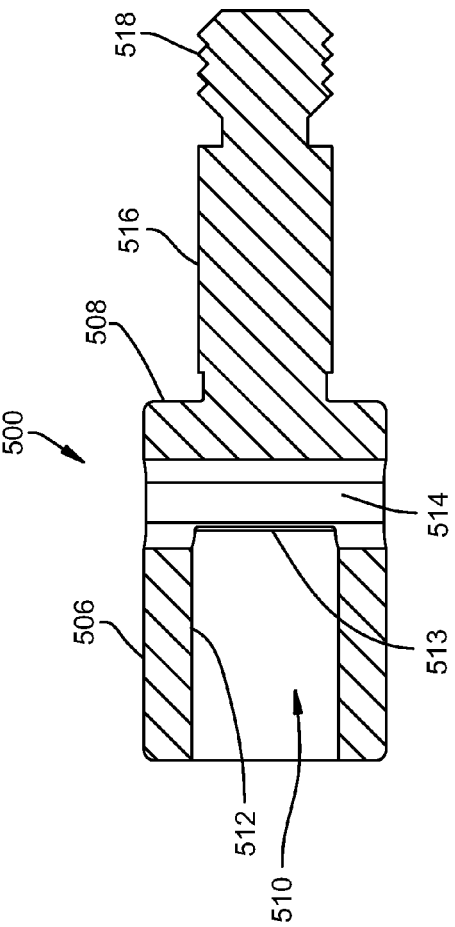
FIG. 22
FIG. 24
FIG. 21

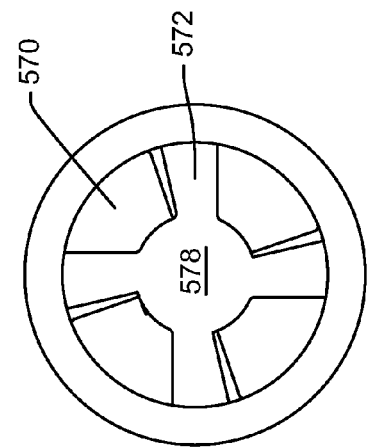
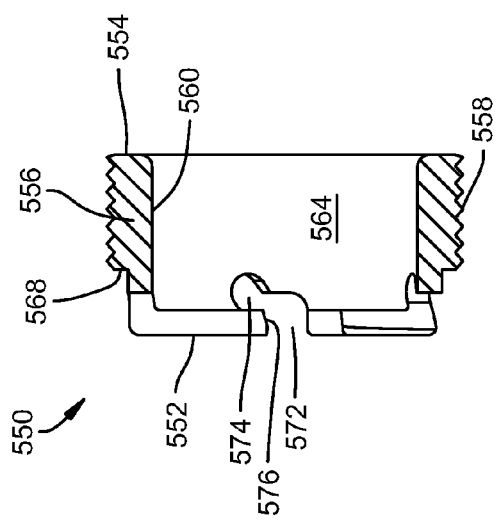
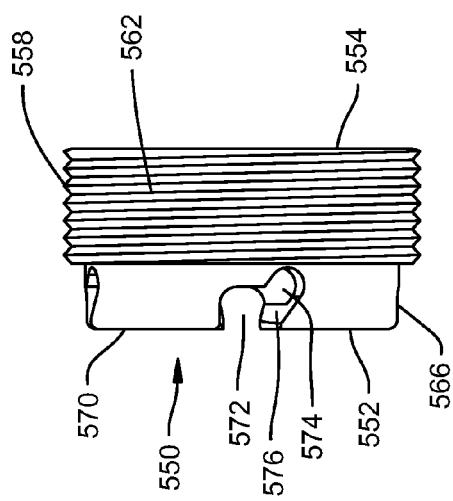

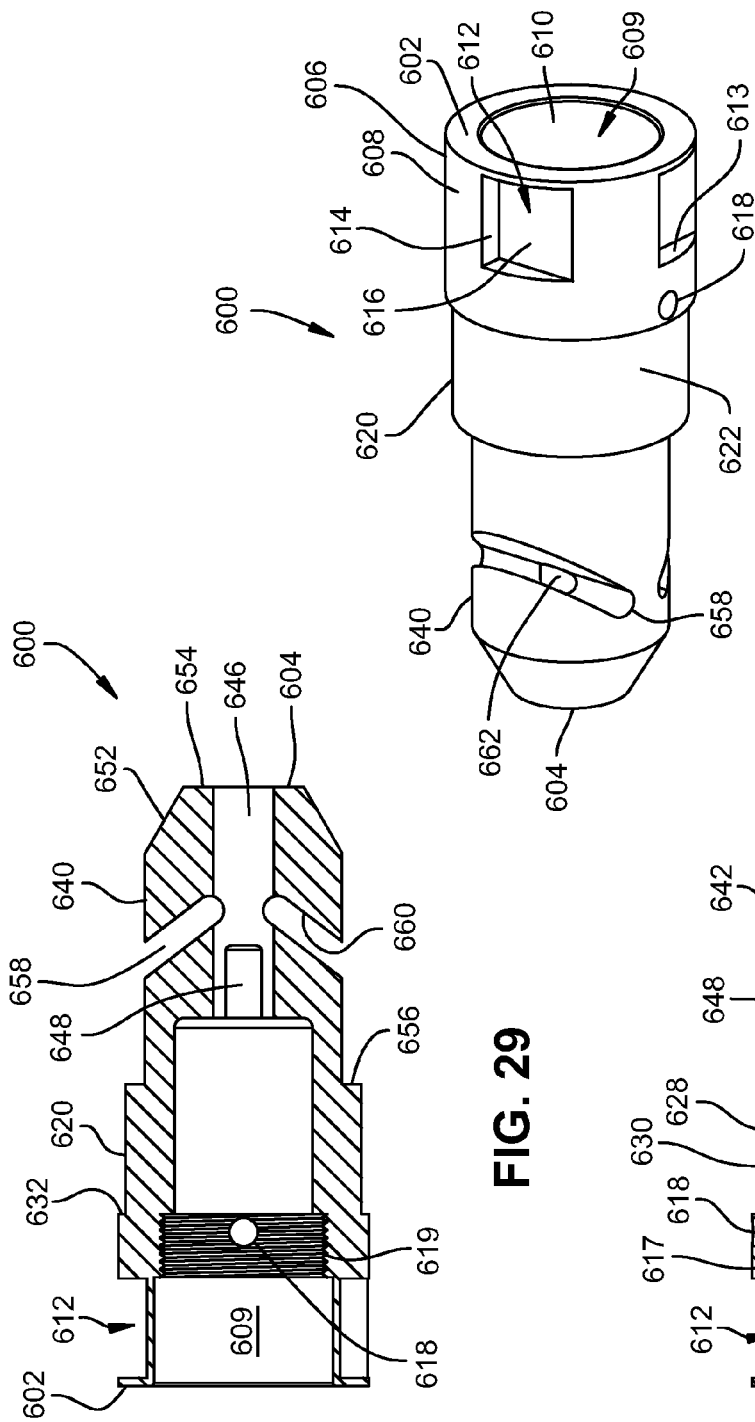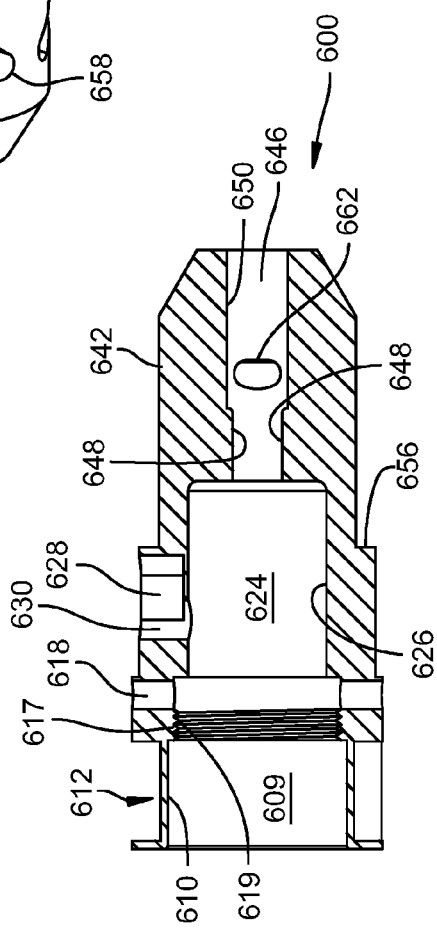

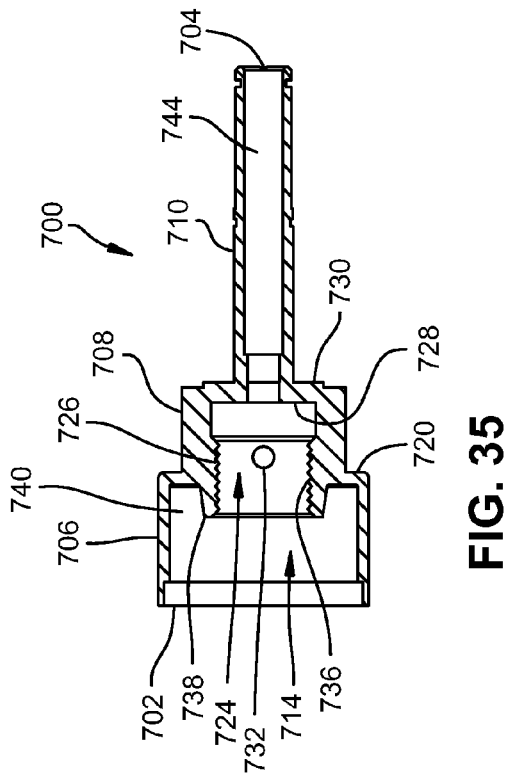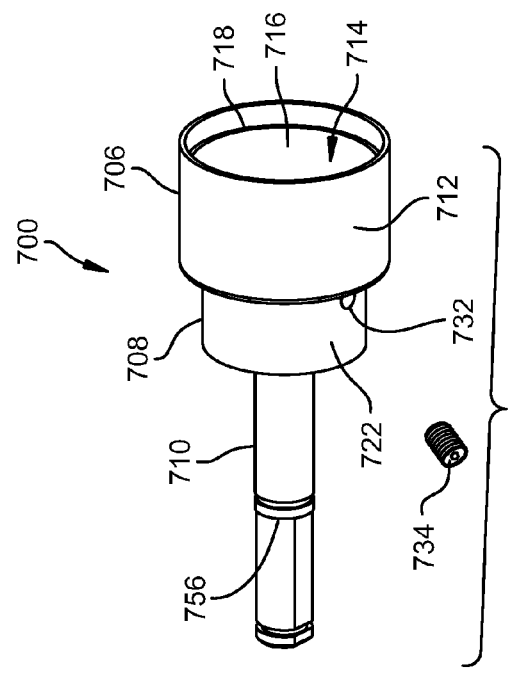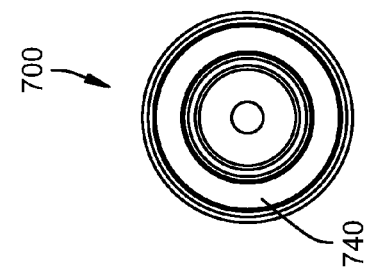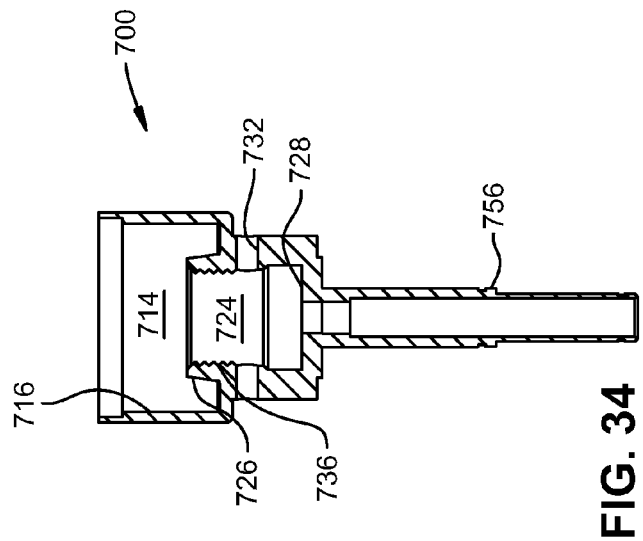

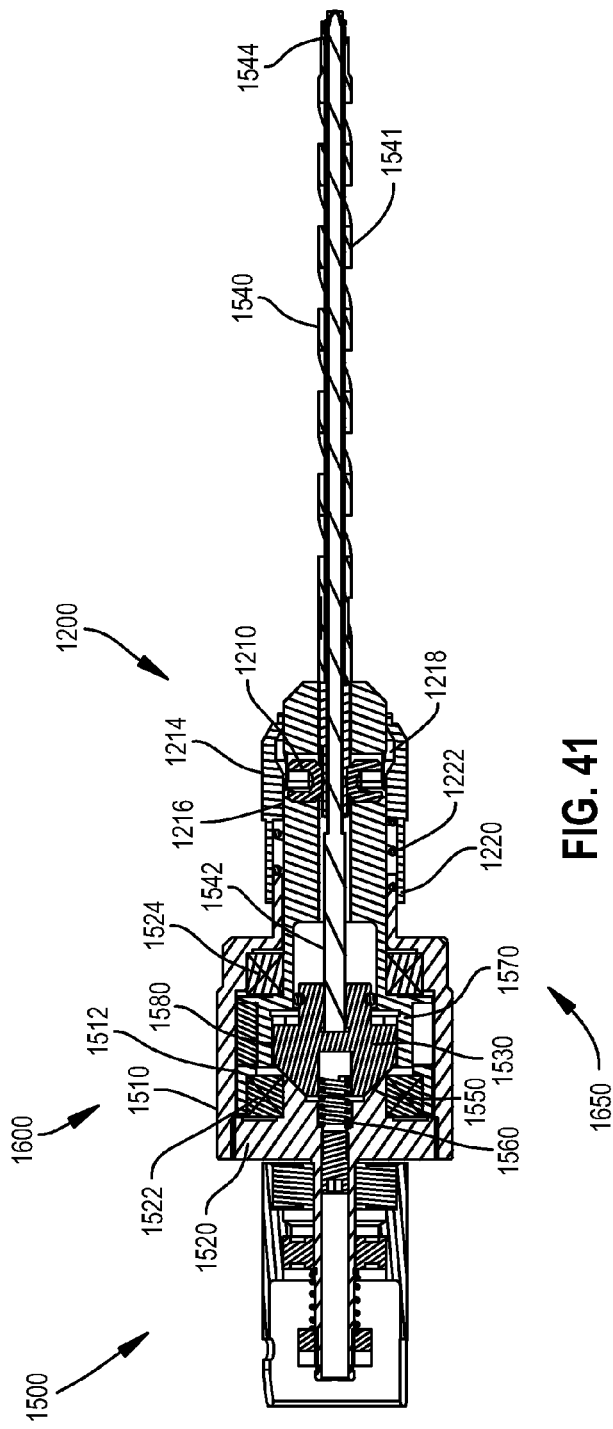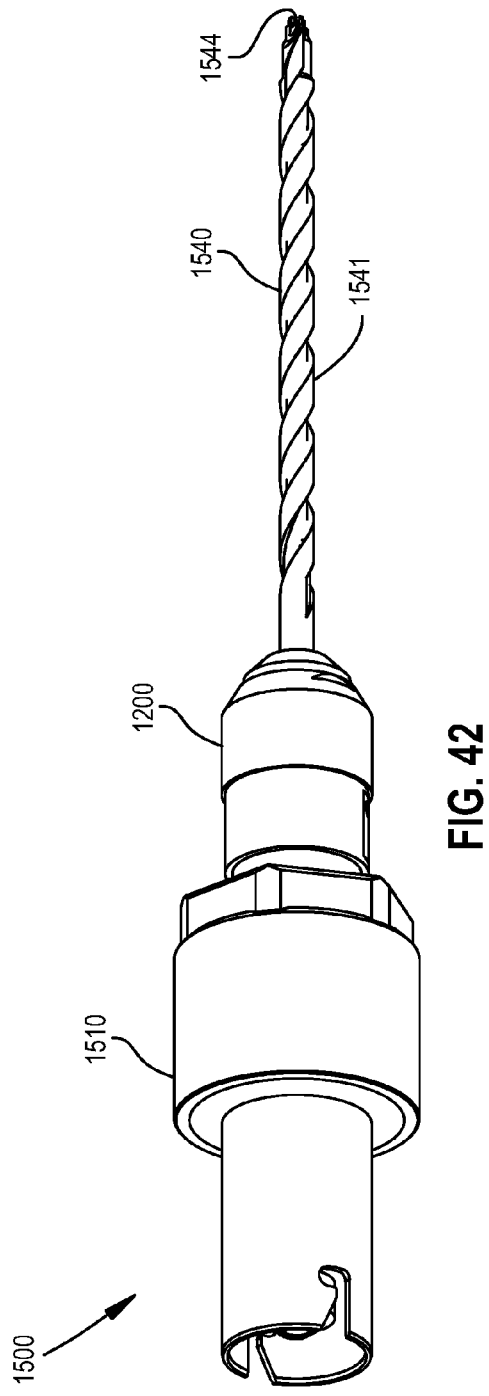
FIG. 41
FIG. 42

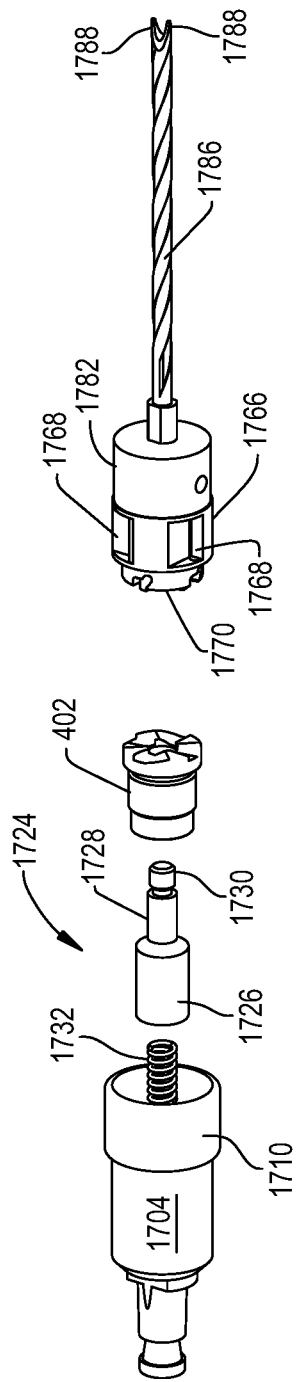
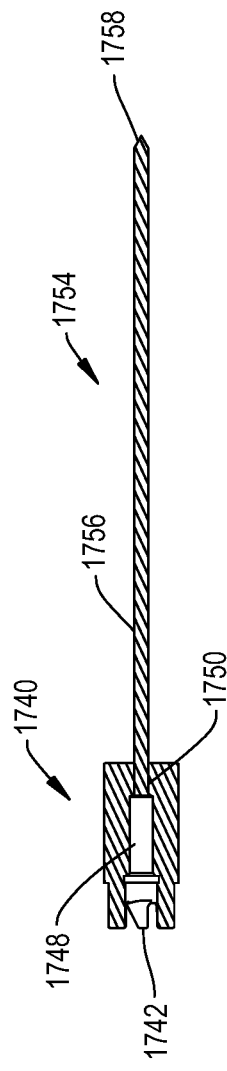
FIG. 45
FIG. 47

SURGICAL DRILL WITH DRIVE SHAFT AND DRILL BIT THAT, AFTER DISENGAGING THE DRILL BIT FROM THE DRIVE SHAFT, ALLOWS THE DRILL BIT TO BE DRIVEN IN REVERSE

RELATIONSHIP TO EARLIER FILED APPLICATION

This application claims priority from U.S. Provisional Pat. App. No. 61/610,779 filed 14 Mar. 2012 the contents of which are explicitly incorporated herein by reference.

FIELD OF THE INVENTION

This invention relates generally to surgical drill used to form a bore in tissue such as bone. More particularly, the drill of the invention disengages upon penetrating through the bone into which the drill bit is inserted and can then be driven in reverse in order to remove the drill bit.

BACKGROUND OF THE INVENTION

In modern surgery, one of the most important instruments available to medical personnel is the powered surgical drill. Typically, this drill comprises a housing in which a motor is secured. The motor has a shaft that is connected to some type of chuck or other coupling assembly attached to the housing. The coupling assembly holds a cutting accessory that is applied to the patient in order to perform a specific medical procedure. Some common cutting accessories are drill bits, burs and reamers. These accessories are used to drill into and/or separate sections of soft tissue and hard tissue, commonly referred to as bone. The ability to use surgical drills to actuate these and other cutting accessories has lessened the physical strain of physicians and other medical personnel that perform these medical procedures. Moreover, most surgical procedures can be performed more quickly and more accurately with powered surgical tools than with the manual equivalents that preceded them.

Surgical drills are often used in certain orthopedic surgical procedures in order to facilitate the repair of fractured and broken bones. These fractures and breaks typically occur as a result of trauma to the bone. In this type of procedure it is practice to fit a pin or screw to the adjacent sections of the bone so as to hold these sections together. In this type of procedure, the drill is used to form a bore hole/holes in the section/sections of the bone in which the pin or screw is to be fitted.

In this type of procedure, the drill bit, while it should extend through the bone, should not be pressed beyond the bone. This is because if the tip of the drill bit, presses through the bone, the tip could damage the soft tissue adjacent the bone. This damage is more likely to occur if the tip, when pressed against the soft tissue, is rotating. This soft tissue, it should be appreciated, includes both neurological tissue and blood vessels. While it is always in the best interest of the patient to avoid damaging any tissue, it is even more important to avoid damaging nerves and blood vessels.

Accordingly, when a surgeon is forming a bore in bone in order to set a pin or a screw, the surgeon must typically use extreme care to ensure that, as soon as possible after the drill bit tip penetrates through the bone, the drill is deactivated.

One means suggested to reduce the extent to which a rotating drill bit is allowed to press into soft tissue adjacent a bone is to provide trauma surgeons with drills similar to the cranial perforators used by neurosurgeons. A cranial perforator is the type used by a neurosurgeon in order to form the initial entrance opening into the skull. A cranial perforator includes a head and inner and outer drills. The inner drill is in the form of a solid cylinder that is fluted at the distal end. The outer drill is in the form of a sleeve that extends circumferentially around the inner drill. Both drill bits extend from the head. The head is attached to handpiece having a motor. Internal to the head both the head and the drill bits have features that, when engaged, causes the drill bits to rotate with the rotation of the head. Also internal to the head is a spring. The spring normally holds at least one of the drills away from the complementary features integral with the head. When the drill bits are pressed against bone, the resistance of the bone pushes the drill bit and head features into engagement. When the perforator is in this state, the rotation of the head results in a like rotation of the drills. The rotational moment and forward force of the drills causes the drills to form the desired bore. When the inner drill, penetrates through the skull, the skull no longer offers resistance to the release action of the spring. The spring pushes the inner drill away from the head. Owing to the engagement of the outer drill with the inner drill, the outer drill also stops rotating. Thus, when the perforator is in this state, the rotation of the head does not cause a like rotation of the drill bits. Since the drills are not rotating when the perforator is in the this state the pressing of the drills against the tissue, the thin soft tissue below the skull does not result in appreciable damage to this tissue. In many versions of the invention the head and drill bits are formed with complementary ramp features. These ramp features facilitate the disengagement of the drills from the head. A more detailed understanding regarding how a cranial perforator operates can be found in the Applicant's Assignee's US Pat. Pub. No. US 2009/0024129 published 22 Jan. 2009, the contents of which are explicitly incorporated herein by reference.

One reason cranial perforators work well for forming bores in the skull is that the skull is relatively thin. Typically the skull has a thickness of 1.5 cm or less. Thus, once the bore is formed, the surgeon, with using only a minimal amount of force, can pull the perforator out of the newly formed bore.

In trauma surgeries and other orthopedic surgeries the surgeon may want to form a bore hole in bone that is relatively thick, having a thickness of 3.0 cm or more. Owing to the tight fit of the drill bit in the bore, it is rather difficult to simply pull the bit out of the bone. If a practitioner uses a large amount of manual force, there is the possibility that the use of this back force, especially if coupled with a back and forth prying action, can damage the bone. This force if strong enough can also damage the drill bit.

To avoid the possibility of this post bore formation bone damage, an orthopedic surgeon typically drives the drill bit in reverse in order to facilitate the backing out of the bit from the bore. However, as mentioned above, once the drills of a cranial perforator penetrate the bone, they are disengaged from the complementary head. Driving the head in reverse does not foster a like rotational movement of the drills. This is why cranial perforators, while useful for preventing damage to the tissue underlying the bone against which they are pressed have not proven particularly suitable for forming the relatively deep bores required by orthopedic surgeons.

Another problem with the use of cranial perforators is that during the formation of a bore, the drill bit may disengage from the motor before the bore is completely formed. The orthopedic surgeon may need to remove the drill and then re-drill the bore again to complete the formation of the bore.

Moreover, once the bore is formed, it is desirable to determine its depth. This aids the surgeon in determining the length of the pin or screw that needs to be fitted in bore. Current depth gauges take the forms of a rod with a distal end step. The rod is placed through the bone bore and moved until the step catches on the bone adjacent the bottom of the bore. The surgeon then reads the depth from a shell to which the rod is slidably mounted. Often these depth gauges are designed so that the step is very small in width, 2 mm or less. This makes positioning the rod so that step catches a time consuming task.

Thus, to perform this measurement, the surgeon must first delicately position the wire to ensure that the hook does not damage tissue underlying the bone. Then, to accurately make the measurement, the surgeon must both carefully position the wire and his/her finger against the wire. Having to carefully perform these steps can add to the overall it takes to perform the procedure.

SUMMARY OF THE INVENTION

This invention is related to a new and useful surgical drill. The assembly of this invention includes a chuck that extends from the powered handpiece. The chuck releasably rotatably couples a drill bit assembly to the handpiece. When the drill bit assembly is pressed against bone, the bit assembly is held in a first engaged state by the chuck. When the drill bit is in this first engaged state, the chuck at least transfers forward rotational motion output by the motor internal to the handpiece to the drill bit. Once the drill bit penetrates the bone, the chuck displaces the drill bit assembly from the first engaged state to a second engaged state. When the drill bit is in the second engaged state, the chuck only transfers reverse rotational motion output by the handpiece motor to the bit assembly.

The chuck of this invention includes an input drive shaft. This is the drive shaft that receives the rotational power output by the shaft integral with the motor. The chuck has two clutches. A first clutch assembly selectively transfers power from the input drive shaft to an inner coupler. The first clutch normally holds the inner coupler in a disengaged state relative to input drive shaft. When the bit assembly is pressed against bone, the bit is exposed to axial resistance, an axial load. This resistance places a displacing force on the clutch that causes this inner coupler to engage with inner drive shaft. In some versions of the invention the rotational moment is only transferred to the inner coupler when the input drive shaft rotates in a first direction. A second clutch transfers power from the input drive shaft to an outer coupler. The second clutch only transfers power from the input drive shaft to the outer coupler when the input drive shaft rotates in a second direction, opposite the first direction.

In some but not all versions of the invention, the invention is used with a drill bit assembly that includes inner and outer drill bits. The inner drill bit is releasably coupled to the inner coupler for rotation. The outer drill bit is releasably coupled to the outer coupler for rotation.

When a drill of this invention is used, the practitioner presses the distal end of the drill assembly against the bone in which a bore is to be formed. The resistance of the bone to the drill bit pushes the inner coupler into engagement with the input drive shaft. When the clutch is in this state, the first clutch transfers both forward rotational motion of the input drive shaft to the inner coupler. The inner coupler, in turn transfers the rotational motion to the inner drill bit.

Upon the bit assembly breaking through the bone, the disengaging force of the first clutch moves the inner coupler out of engagement with the input drive shaft. The bit assembly therefore stops rotating. This substantially minimizes damage to the tissue adjacent the bore opening formed by the drill.

The second clutch only engages when the input drive shaft is rotated in the reverse direction. Consequently, when the surgeon is ready to withdraw the drill bit from the bone, the drill is reverse rotated. The subsequent reverse rotation of the drill bit assembly reduces the axial load that needs to be placed on the drill bit assembly in order to withdraw the assembly from the newly formed bore.

In some, but not all versions of the invention, the chuck is removably attached to the associated handpiece that contains the motor.

BRIEF DESCRIPTION OF THE DRAWINGS

The invention is pointed out with particularity in the claims. The above and further features and advantages of this invention are understood from the following Detailed Description taken in conjunction with the accompanying drawings in which:

FIG. 9 is another cross-sectional view of the chuck assembly;

FIG. 10 is a left side view of the chuck assembly;

FIG. 13 is a front view of a drive cap;

FIG. 14 is a cross-sectional view of the drive cap;

FIG. 15 is a side view of the drive cap;

FIG. 19 is a perspective view of the inner coupler;

FIG. 21 is a front view of a plunger;

FIG. 22 is a side view of the plunger;

FIG. 24 is a cross-sectional view of the plunger;

FIG. 25 is a cross-sectional view of a retaining cap;

FIG. 26 is a side view of the retaining cap;

FIG. 28 is a front view of the retaining cap;

FIG. 29 is a cross-sectional view of the outer coupler;

FIG. 30 is another cross-sectional view of the outer coupler;

FIG. 31 is a perspective view of the outer coupler;

FIG. 33 is a front view of an input drive shaft;

FIG. 34 is a cross-sectional view of the input drive shaft;

FIG. 35 is another cross-sectional view of the input drive shaft;

FIG. 36 is a perspective view of the input drive shaft;

FIG. 41 is a cross-sectional view of an alternative embodiment of a chuck assembly in accordance with the present invention;

FIG. 42 is a perspective view of the chuck assembly of FIG. 41;

FIG. 45 is an exploded view of the surgical drill of FIG. 43;

FIG. 47 is a cross sectional view of the input drive shaft of the surgical drill of FIG. 43;

DETAILED DESCRIPTION

I. Handpiece

Figure 1:
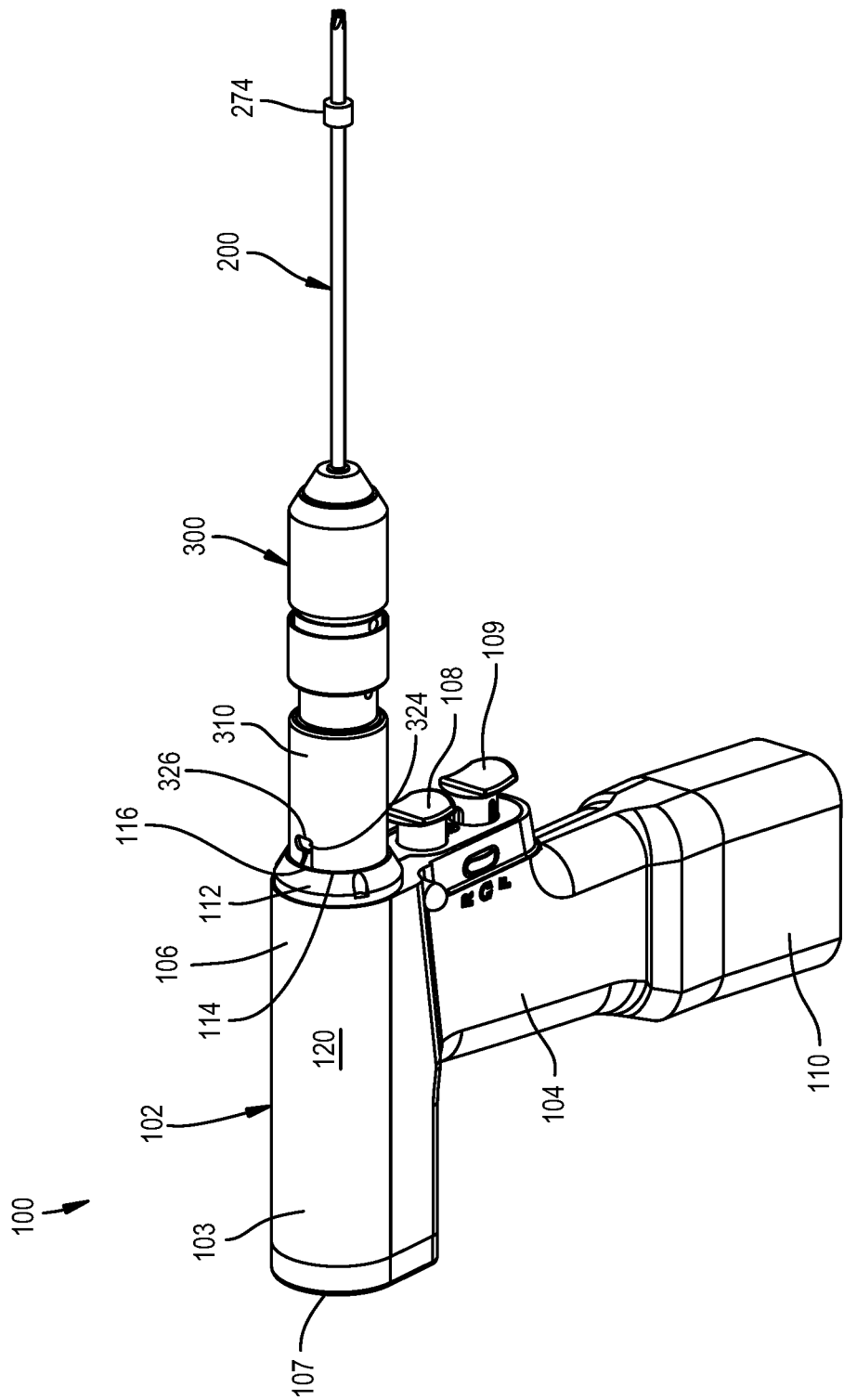
FIG. 1 is an overall perspective view of a powered rotary surgical drill having a chuck with two clutches in accordance with the present invention.
Figure 2:
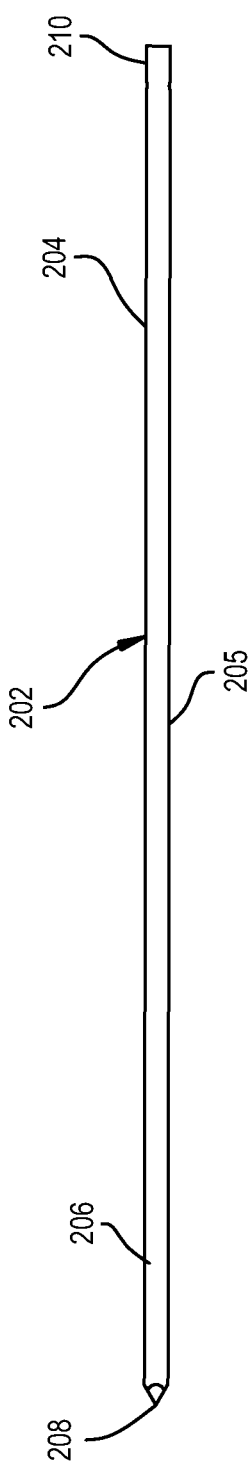
FIG. 2 is a side view of an inner drill bit.
Figure 3:
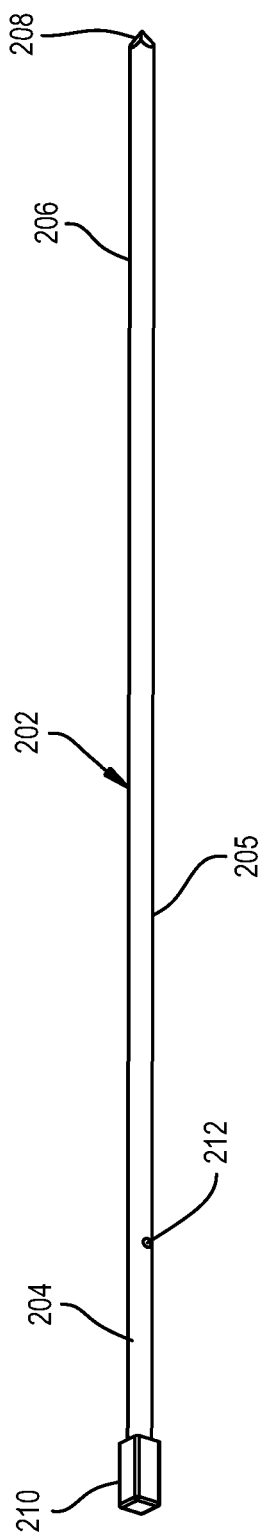
FIG. 3 is a perspective view of the inner drill bit.
Figure 4:
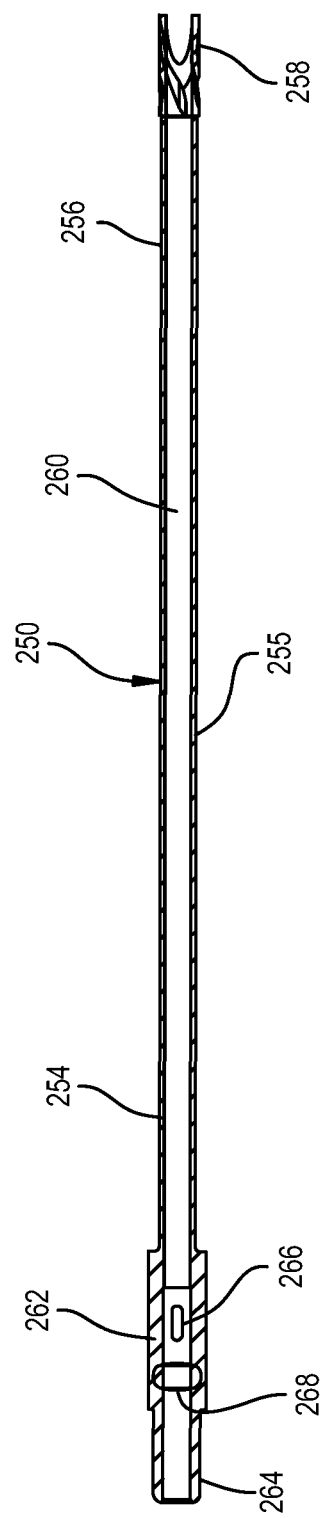
FIG. 4 is a cross-sectional view of an outer drill bit.
Figure 5:
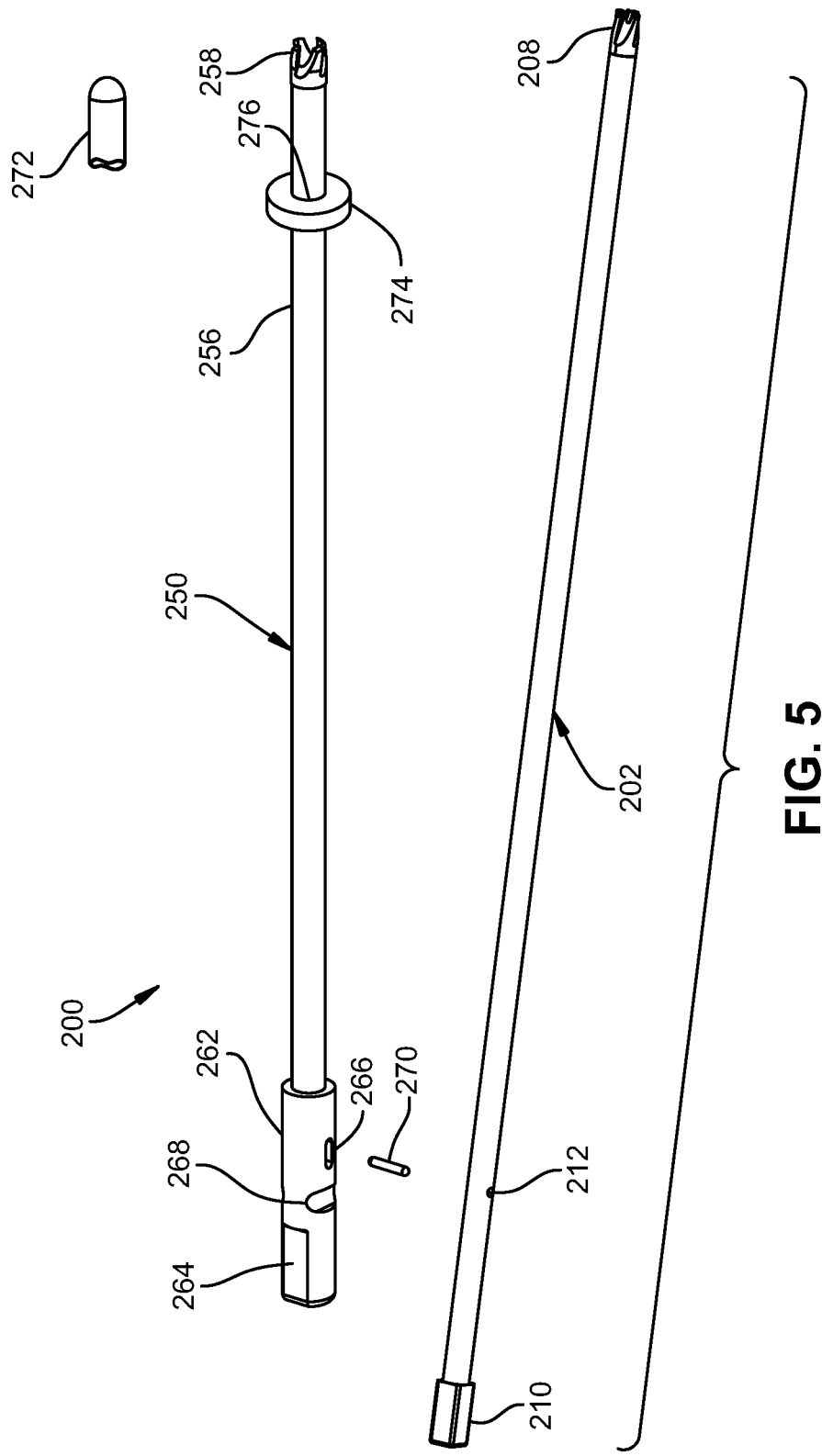
FIG. 5 is an exploded perspective view of a drill bit assembly.

FIG. 1 illustrates a rotary surgical drill 100 in accordance with the present invention. Rotary surgical drill 100 has a handpiece 102. Handpiece 102 has an upper housing 103 and a handle 104 that extends downwardly from upper housing 103. Upper housing 103 is generally cylindrical in shape and has a distal end 106 and a proximal end 107. "Distal", it shall be understood to mean away from the surgeon holding the drill, towards the surgical site to which the surgical drill 100 is directed. "Proximal", means towards the surgeon and away from the surgical site. Upper housing 103 has an internal cavity 120. A rotary electric motor (not shown) is mounted in cavity 120. Handle 104 is generally in the form of a pistol grip. In one embodiment, the motor is a DC motor. In another embodiment the motor can be an AC motor, or a pneumatic or hydraulically driven motor.

Handle 104 allows a user to grasp and manipulate the rotary surgical drill 100. A forward trigger switch 109 and a reverse trigger switch 108 extends distally forward from the front face of handle 104. A control circuit internal to the housing 103, (not illustrated and not part of this invention) monitors the actuation of the trigger switches 108 and 109. Based on the extent to which the trigger switches 108 and 109 are depressed, the control circuit selectively energizes the motor to cause the output shaft to rotate at the desired speed. A rechargeable battery 110 is removably attached to the bottom end of handle 104. Battery 110 supplies power to rotary surgical drill 100. A cone shaped outer ring 112 is mounted to housing end 106. An opening 114 is defined in ring 112. Opening 114 opens into and is contiguous with internal cavity 120. A spring loaded pin (not illustrated) extends perpendicularly downward from the upper most point of ring 112.

Drill 100 also includes a drill bit assembly 200 and a chuck assembly 300. Drill bit assembly consists of the drill bits that are driven into the bone. Chuck assembly 300 retains bit assembly 200 releasably holds the drill bit assembly 200 to the handpiece 102 for actuation by the handpiece.

II. Drill Bit Assembly

With reference to FIGS. 2-5, features of drill bit assembly 200 are shown. Drill bit assembly 200 includes an inner drill bit 202 and an outer drill bit 250. Inner drill bit 202 is generally elongated and cylindrical in shape. Outer drill 250 is generally elongated and tube shaped and is disposed over inner drill 202. The inner bit 202 has a proximal end 204, center section 205 and a distal end 206. The inner bit 202 is formed with cutting flutes 208 at distal end 206. A square shaped drive head or member 210 extends outwardly from proximal end 204. Aperture 212 extends across the diameter of inner bit 202.

The outer bit 250 is in the form of an elongated tubular shaft 255 that has a proximal end 254 and a distal end 256. The outer bit 250 is formed with cutting flutes 258 at distal end 256. In many versions of the invention, outer bit 250 is formed so that cutting flutes 258 extend radially outwardly beyond the outer surface of bit shaft 255. In some versions of the invention, maximum outer diameter of the cutting flutes 258 is 0.2 to 0.4 mm greater than the outer diameter of shaft.

A bore 260 extends through the length of shaft 255. An annular flange 262 extends proximally from shaft proximal end 254. Flange 262 terminates with flat sections 264 on opposite sides of flange 262. A pair of diametrically opposed slots 266 are located in flange 262. Elongated slots 266 are defined in flange 262 and extend parallel with the longitudinal axis of outer bit 250. A pair of diametrically opposed grooves 268 are defined in flange 262. Grooves 268 extend perpendicular to the longitudinal axis of outer bit 250.

When drill bit assembly 200 is assembled, inner bit 202 is slip fit into outer bit bore 260. The distal end of bore 260 is open. Inner drill bit 202 thus extends slightly out through the distal end of bore 260. The drive head 210 abuts the proximal face of flange 262. A pin 270 extends through one slot 266, aperture 212 and into the second slot 266. The pin 270 is press fit in aperture 212. Pin 270 retains inner bit 202 within outer bit 250 during shipping and handling of assembly 200. Pin 270 and slots 266 allow a slight amount of longitudinal and rotational motion of inner bit 202 relative to outer bit 250. Pin 270 can slide within slots 266 between the ends of slot 266. Pin 270 also rotates within slots 266 between the sides of slot 266. Pin 270 and slots 266 allow a slight amount of rotation from 1 to 10 degrees to occur between inner drill bit 202 and outer drill bit 250.

Drill bit assembly 200 also includes a protective cap 272 that is press fit over cutting flutes 258. Cap 272 protects cutting flutes 208 and 258 from damage and protects and surfaces that come into contact with cutting flutes 208 and 258 from damage during shipping and handling.

A depth gauge 274 is mounted around the outer circumference of outer bit 250 towards distal end 256. Depth gauge 274 has a center bore 276. Depth gauge 274 can be formed from any suitable material such as plastic or elastomer. The material from which gauge 274 is formed should be able to withstand the frictional heat that is generated during the bore formation process. Depth gauge 274 is press-fit over outer bit 250 by sliding cutting flutes 258 at distal end 256 through bore 276. Depth gauge 275 is dimensioned to have an interference fit to outer bit 250. Depth gauge 274 slides along the outer circumference of outer bit 250 as a bore is formed by drill bit assembly 200.

III. Chuck Assembly

FIGS. 6A-12 illustrate features of chuck assembly 300. Chuck assembly 300 comprises a linear clutch assembly 400, a rotary clutch assembly 1000 and a drill bit retainer assembly 1200. Linear clutch assembly 400 has an inner coupler 450 that can be selectively engaged with a drive cap 402.

Figure 6A:
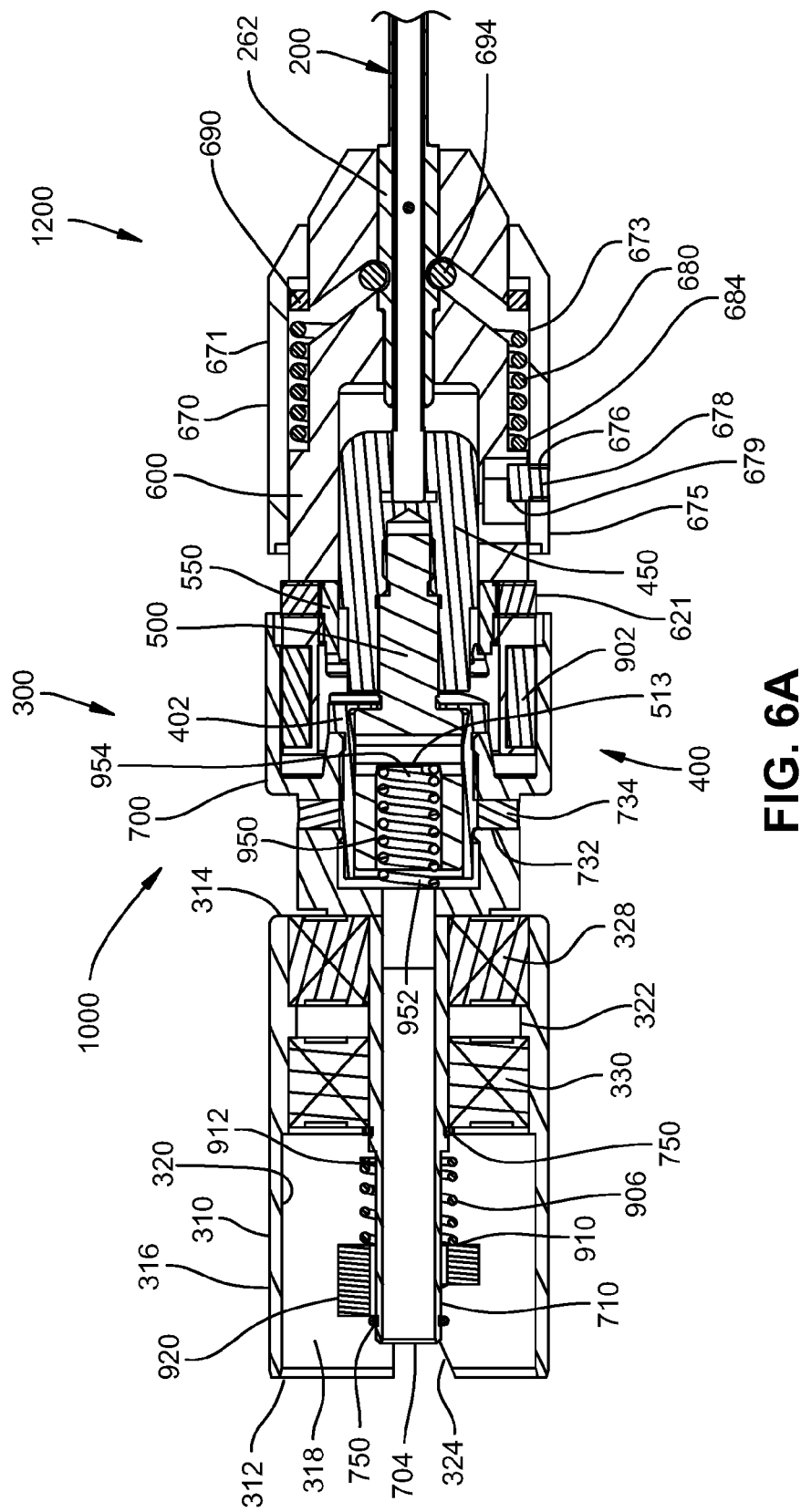
FIG. 6A is a cross-sectional view of a chuck assembly in accordance with the present invention.
Figure 6B:
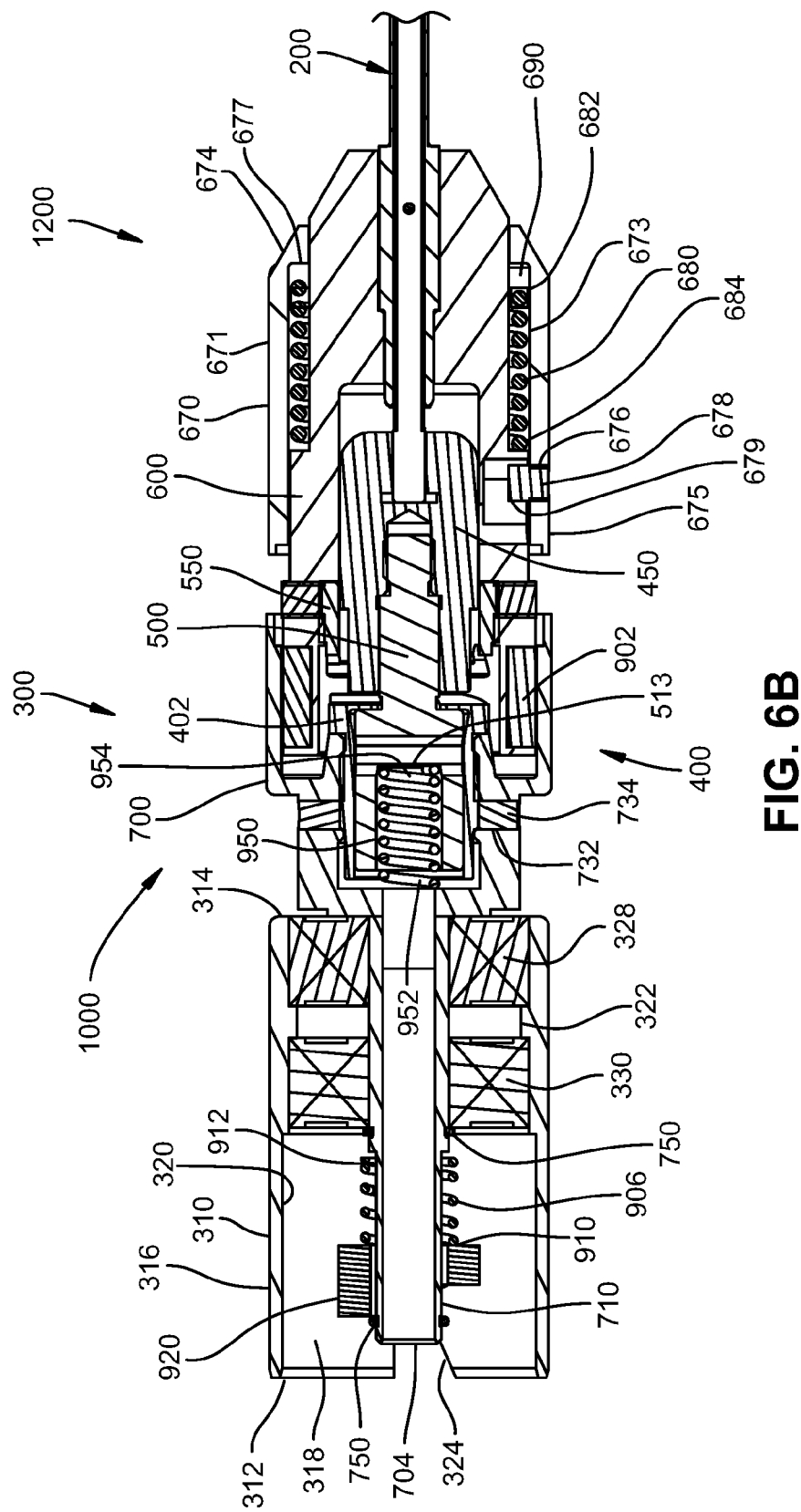
FIG. 6B is another cross-sectional view of the chuck assembly.
Figure 7:
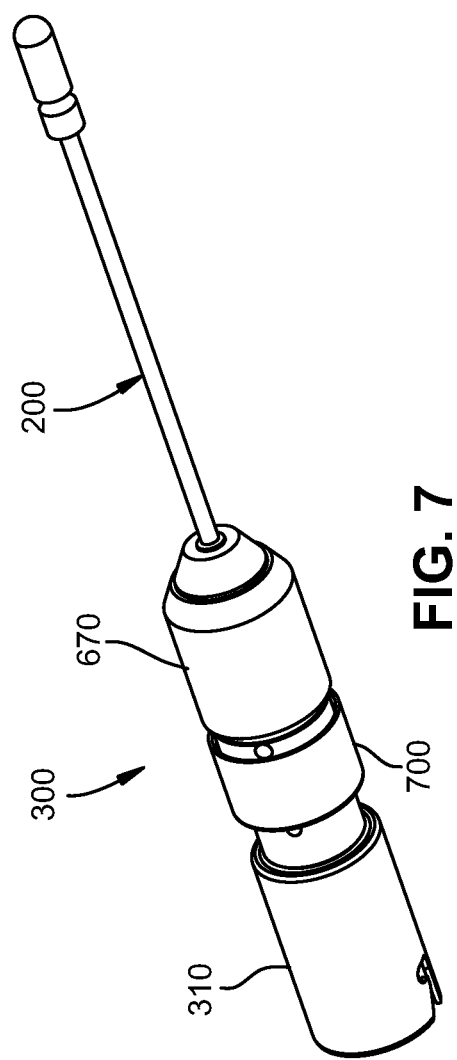
FIG. 7 is a perspective view of the chuck assembly.
Figure 8:
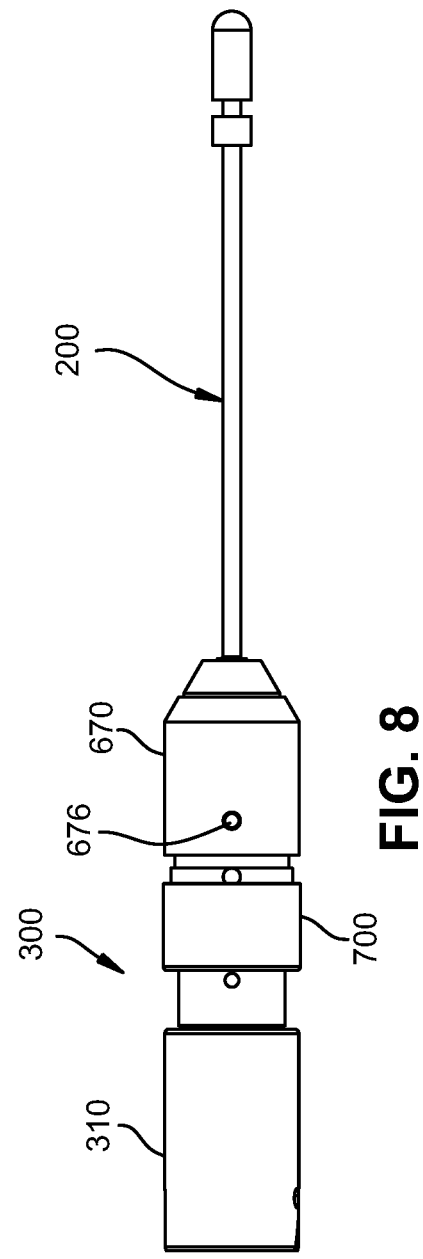
FIG. 8 is a right side view of the chuck assembly.
Figure 11:
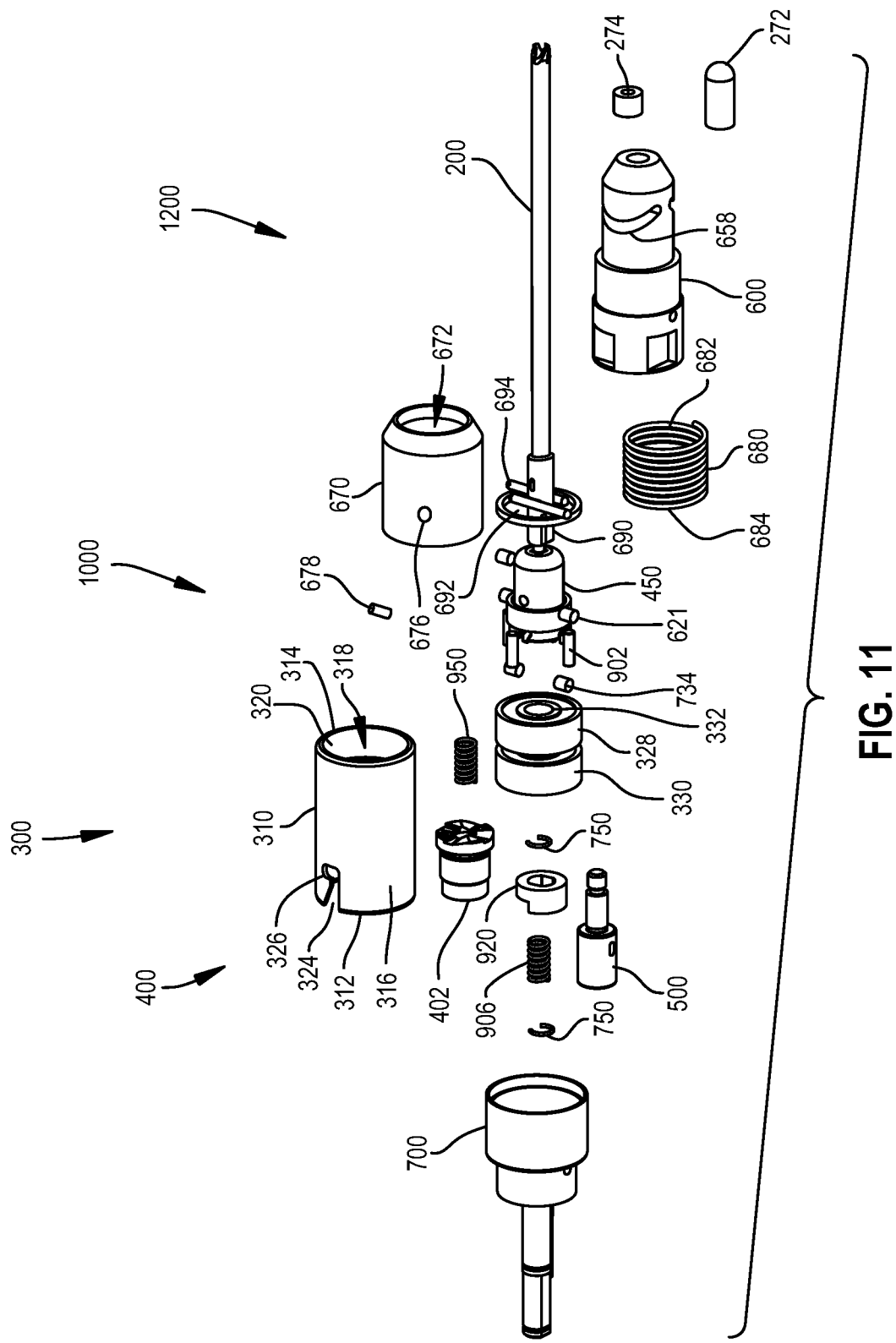
FIG. 11 is an exploded perspective view of the chuck assembly.
Figure 12:
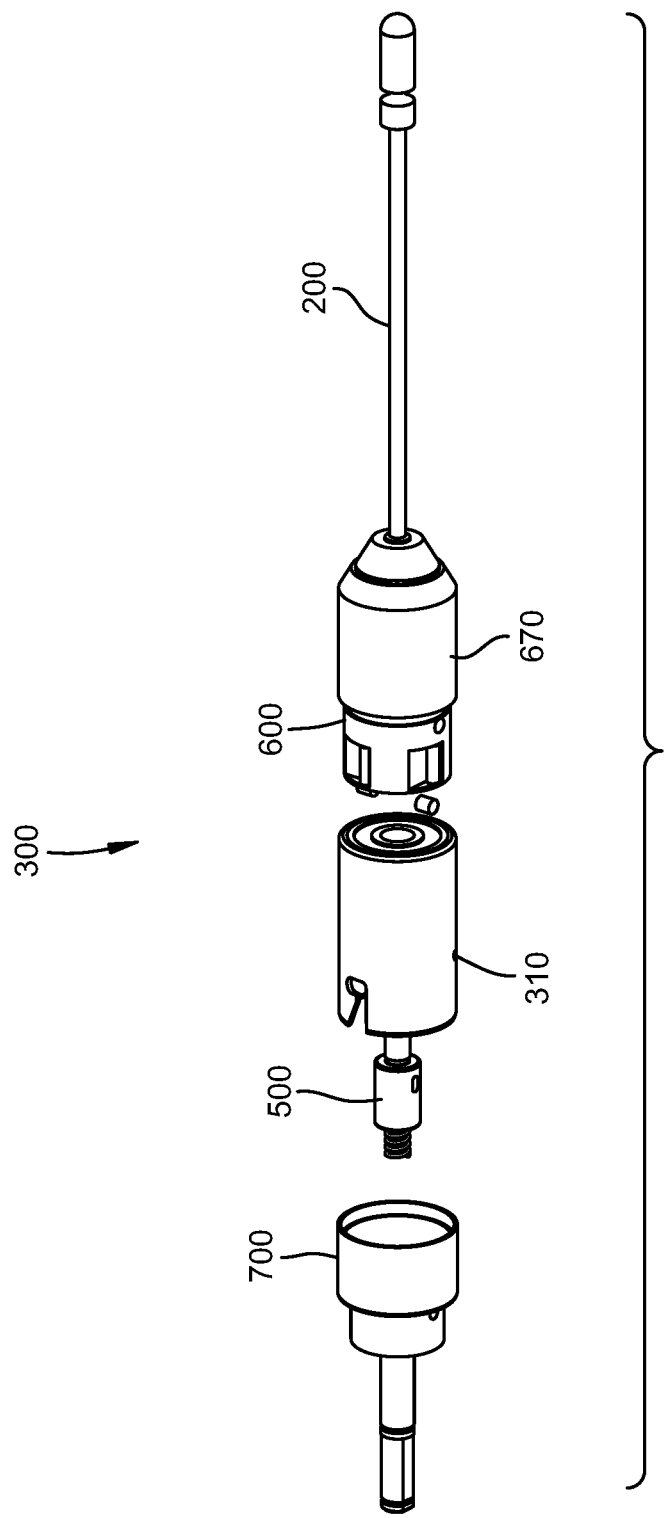
FIG. 12 is a partially assembled perspective view of the chuck assembly.
Figure 16:
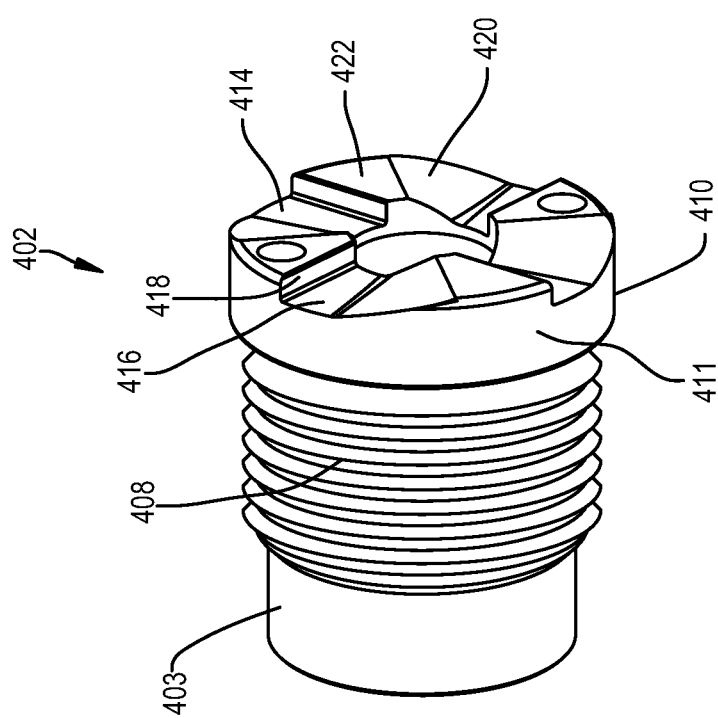
FIG. 16 is a perspective front view of the drive cap.
Figure 20:
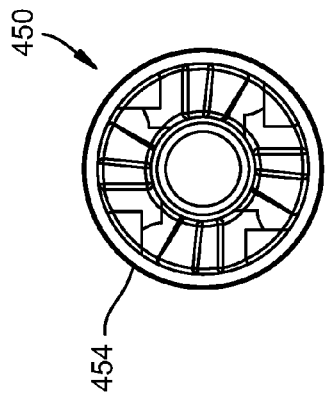
FIG. 20 is a front view of the inner coupler.
Figure 17:
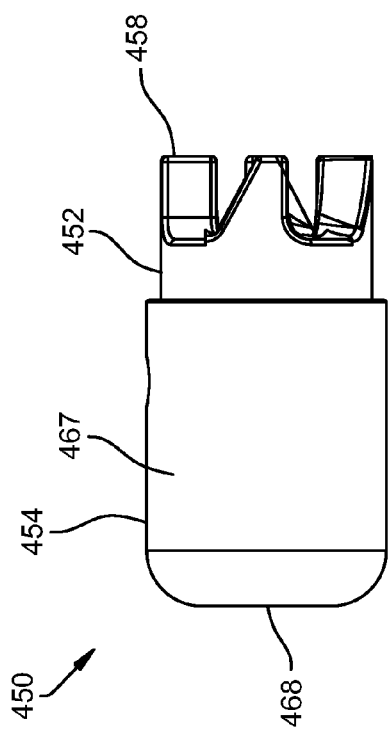
FIG. 17 is a side view of the inner coupler.

Referring to FIGS. 6A, 6B and 11, end cap 310 is cylindrical in shape and has a proximal end 312 and a distal end 314. End cap 310 is formed from a single piece of metal. End cap 310 has an outer annular surface 316. A bore 318 extends through end cap 310 and defines an inner annular surface 320. An annular rib 322 extends into bore 318 and is spaced from distal end 314. An arcuate V-shaped cutout 324 is located in end cap 310 and extends from proximal end 312 towards distal end 314 and terminates in an arcuate slot 326. Cutout 324 is contiguous with slot 326.

End cap 310 and chuck assembly 300 are attached to handpiece 102 (FIG. 1) by inserting end cap proximal end 312 into handpiece opening 114 so that the spring loaded handpiece pin 116 aligned with cutout 324. As end cap 310 is moved in a proximal direction into opening 114, pin 116 will contact the base of slot 326. As a consequence of the spring loading of the handpiece pin in the slot, the chuck is releasably attached to the handpiece 102.

Bearings 328 and 330 are seated in bore 318. Bearing 328 is seated in bore 318 with the outer proximal surface of bearing 328 resting on annular rib 322. Bearing 330 is seated in bore 318 with the outer distal surface of bearing 330 resting on annular rib 322. Bearings 328 and 330 each have a bore 332 extending there through.

Turning now to FIGS. 13-16, drive cap 402 is shown. Drive cap 402 is formed from a single piece of metal. Drive cap 402 includes a tube like sleeve 403 having an inner annular wall 404 that defines a cylindrical bore 405 within cap 402. The drive cap 402 is formed such that inner wall 404 has a constant diameter and extends from the proximal end of the sleeve 403 substantially the entire length of the sleeve. The outer surface of sleeve 403 has a raised annular rib 406 with external threads 408. Sleeve 403 is dimensioned to be fitted into input drive shaft bore 724 (FIG. 35) so that internal threads 736 (FIG. 35) and external threads 408 are engaged to hold the drive cap 402 in a static position within input drive shaft 700. Drive cap 402 has a proximal facing end 407 and a distal facing end 409.

The drive cap 402 has a disk shaped end plate 410 with an annular side wall 411 and a proximal facing end wall 415. The end plate 410 is disposed over the distal end of sleeve 403. While the end plate 410 is generally circular, the drive cap 402 is formed such that the end plate 410 has a center located through hole 412. Hole 412 is coaxial with bore 405. Drive cap 402 is further formed so that the end plate 410 has a larger diameter than the diameter of sleeve 403.

The drive cap 402 is also constructed so that adjacent the end plate 410, sleeve 403 has a distal inner wall section 413 that extends forward from inner wall 404. Inner wall section 413 is different from inner wall 404 in that, as wall section 413 extends distally forward, the wall section 404 flares outwardly. Inner wall 413 defines an undercut in the distal end of the sleeve 403 immediately adjacent end plate 410.

Drive cap 402 has an outer, distally directed face of the end plate 410 with four equangularly spaced apart notches 414. The base of each notch 414 is defined by a base surface 416. A vertical wall 418 extends perpendicularly upward from one end of the base surface 416 to define one end of the notch 414. The opposed end of the notch 414 is defined by a ramp 420. Each ramp 420 extends helically upwardly and arcuately away from the base surface 416 with which it is associated.

Each ramp 420 terminates at a raised face 422. The raised face 422 terminates at the edge of the wall 418 associated with the adjacent notch 414. A pair of diametrically opposed bores 424 are located in two of the raised faces 422 and extend through end plate 410 into bore 405. Bores 424 are used during assembly.

The inner coupler 450, described with reference to FIGS. 17-20 is generally cylindrical in shape and has two coaxial sections 452 and 454, with different diameters. There is a proximal section 452 and a distal section 454. Proximal section 452 has a diameter slightly less than that of distal section 454. Proximal section 452 defines a proximally directed face 456. Inner coupler 450 is formed from a single piece of metal.

Face 456 is divided into four sections by four equangularly spaced apart, proximally extending legs 458. Each leg 458 is shaped to define a first vertical surface 460 that extends perpendicularly away from the adjacent section of the proximally directed face 456. A curved transition surface 462 extends between each face section 456 and the adjacent leg surface 460. Vertical surface 460 ends at a proximal facing end surface 464 that is perpendicular to vertical surface 460.

The four leg end surfaces 464 are the four butt end surfaces of the inner coupler 450. Extending downwardly from each of the leg end surfaces 464 is a third leg surface or ramp 466. Ramps are helical in shape. Each ramp 466 extends downwardly and arcuately away from the adjacent end surface 464. Each ramp 466 has a slope that is constant from the curved surface 462 to the end surface 464 between which the ramp extends. In some versions of the invention, this angle of the ramp, relative to the longitudinal center axis of the inner coupler is between 35 and 50°.

Distal section 454 has an outer wall 467 that curves to a distal end face 468. A square shaped bore 470 extends through face 468 into inner coupler 450 and faces in a proximal direction. Bore 470 is adapted to receive square drive head or member 210 of inner bit 202. Rotation of inner coupler 450 causes a like rotation of inner bit 202. An annular recess 472 is defined at the proximal end of bore 470.

Figure 23:
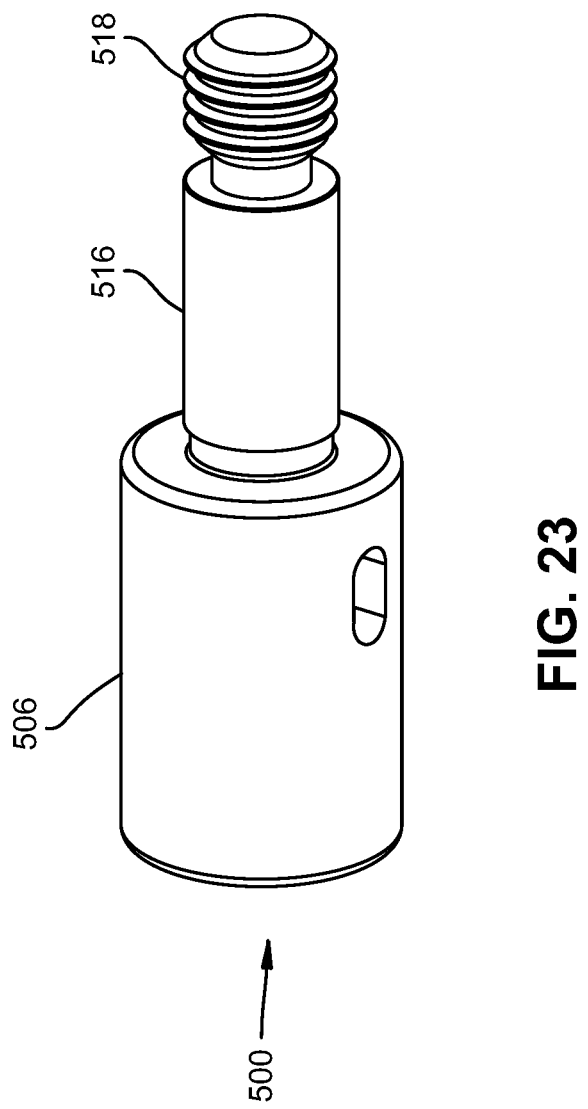
FIG. 23 is a perspective view of the plunger.
Figure 27:
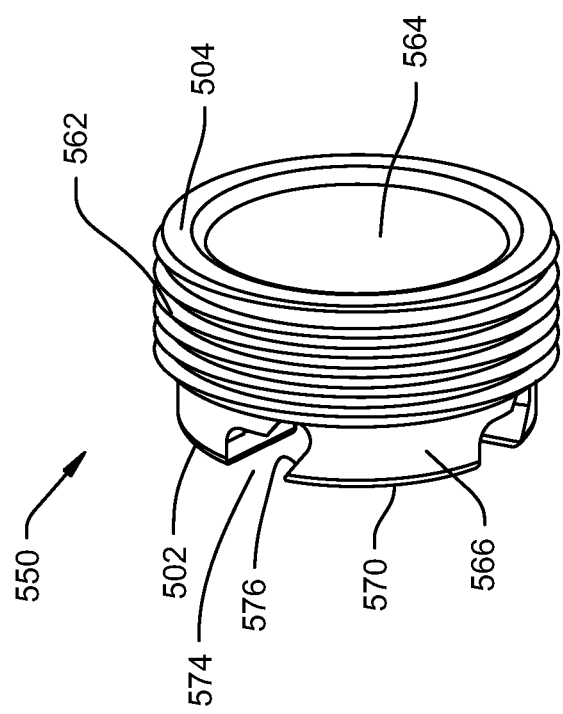
FIG. 27 is a perspective view of the retaining cap.

Inner coupler 450 is further formed to have a number of coaxial bore sections that extend distally from end surface 464. Bore 474, is defined by the inner arcuate surfaces of legs 458. Bore 474 is dimensioned to closely slip fit receive plunger distal stem section 516 (FIG. 23). Contiguous with and immediately adjacent bore 474 there is another bore 476. Bore 476 has a diameter that is slightly greater than the diameter of bore 474. Contiguous with and immediately adjacent bore 476 there is another bore 478. Bore 478 has a diameter that is smaller than the diameters of bores 474 or 476. Bore 478 has interior threads 480 on an inner annular surface that are adapted to mate with threads 524 (FIG. 22) of plunger distal stem section 518 (FIG. 22).

After the inner coupler 450 is coupled to the plunger 500, the engagement of threads 480 and threads 524 retains the inner coupler 450 and the plunger 500 together. Plunger stem section 516 is seated in bore 474. The components are further constructed so that, upon assembly, the legs 458 are juxtaposed to and spaced from the adjacent distally directed end plate 410 of drive cap 402.

A threaded aperture 482 extends perpendicularly from outer surface 467 into bore 478. Threads are located on the inner annular surface of aperture 482. Aperture 482 is dimensioned to receive a set screw 484. When set screw 484 is seated in aperture 482, set screw 484 engages plunger distal stem section 518 locking the inner coupler 450 and the plunger 500 together.

Referring to FIGS. 21-24, plunger 500 is illustrated. Plunger 500 is formed from a single piece of metal. Plunger 500 is generally cylindrical in shape. Plunger 500 has a proximal end 502 and a distal end 504. A cylindrical shaped head 506 is located on the proximal portion of the plunger. Head 506 has an outer annular surface 507 and defines an inwardly directed distal facing step 508 toward the center of the plunger. A bore 510 extends in a distal direction into head 506 from proximal end 502 and has an inner annular surface 512. Bore 510 terminates in an annular end wall 513 that faces in a proximal direction. A slot 514 extends through head 506 perpendicular to the longitudinal axis of the plunger. Slot 514 is oval in cross-section. As seen in FIG. 21, end wall 513 is split into two opposed semi-circular halves by slot 514. Slot 514 is used during assembly.

Plunger head 506 is dimensioned to closely slip fit into drive cap bore 405 such that drive cap inner wall 404 is adjacent plunger outer surface 507 and plunger step 508 is adjacent the end wall 415.

Extending distally from the head 506, the plunger 500 has coaxial annular proximal and distal stem sections 516 and 518, respectively. The proximal stem section 516 extends in a distal direction from step 508. Distal stem section 518 is located at distal end 504. A neck 520 is located between head 506 and proximal stem section 516. Another neck 522 is located between proximal stem section 516 and distal stem section 518. External threads 524 are located on the outer annular surface of distal stem section 518.

Proximal stem section 516 is mounted to extend through drive cap hole 412. The proximal stem section 516 has a diameter slightly less than that of the drive cap through hole 412. Proximal stem section 516 is dimensioned to slip fit into inner coupler bore 474. Distal stem section 518 is seated in bore 478. Inner coupler internal threads 480 mate with distal stem section external threads 524 such that plunger 500 and inner coupler 450 are connected. Set screw 484 is rotated along threaded bore 482 until the end of set screw 484 jams into distal stem section threads 518. Set screw 484 locks inner coupler 450 to plunger 500. When set screw 484 is seated in bore 482, the outer end of the set screw is below the outer surface 467 of the inner coupler.

A retaining cap 550, illustrated in FIGS. 25-28, is attached to the proximal end of the below described outer coupler 600. Retaining cap 550 is formed from a single piece of metal. Retaining cap 550 is generally cylindrical in shape. Retaining cap 550 has a proximal end 552 and a distal end 554. Retaining cap 550 has a cylindrical wall 556 with an outer annular surface 558 and an inner annular surface 560. External threads 562 are defined in outer annular surface 558. A bore 564 extends through retaining ring 550. The distal end of inner surface 560 is chamfered where it abuts distal end 504.

Retaining cap 550 has a proximal section 566 with a small diameter than wall 556. A step 568 is defined between proximal section 566 and wall 556. Proximal section 566 is partitioned into four arcuate ribs 570 that are separated by slots 572 and surround an opening 578. Opening 578 is contiguous with bore 564. Slots 572 extend between bore 564 and the outer annular surface of proximal section 566. Secondary slots 574 are located adjacent to slots 572 and are partially defined by a ramp surface 576.

The ramp surface 576 allows a small amount of rotation between 2 to 10 degrees to occur between the inner bit 202 and the outer bit 250. Ramp surface 576 also allows for legs 458 of inner coupler 450 to disengage from notches 414 of drive cap 402.

Retaining cap 550 is assembled to the outer coupler 600. Retaining cap external threads 562 mate with the outer coupler internal threads 619 (FIG. 29) such that retaining cap 550 is affixed to outer coupler 600. During assembly, inner coupler 450 is slip fit into retaining cap bore 564 such that proximal section 452 is adjacent inner surface 560. Inner coupler 450 can move in a distal direction away from retaining cap 550. Inner coupler legs 458 extend through slots 572 in order to make contact with drive cap 402.

FIGS. 29-32 show details of outer coupler 600. Outer coupler 600 is formed from a single piece of metal. Outer coupler 600 is generally cylindrical in shape. Outer coupler 600 has a proximal end 602 and a distal end 604. Outer coupler 600 has three adjacent cylindrical sections, base section 606, center section 620 and top section 640. Center section 620 has a diameter that is less than the diameter of base section 606. Top section 640 has a diameter that is less than center section 620.

Base section 606 has an outer annular surface 608 and a bore 609 defining an inner annular surface 610. Four indentations 612 are defined in outer annular surface 608. Indentations 612 are spaced equidistant apart on base section 606. Indentations 612 are defined by side walls 613, an end wall 614 and a ramp surface 616. End wall 614 is perpendicular to outer annular surface 608. Ramp 616 extends from outer annular surface 608 to the bottom of end wall 614. An annular rim 617 extends into bore 609 from inner annular wall 610. Internal threads 619 are formed on rim 617. Retaining cap 550 is seated in bore 609 and affixed to outer coupler 600 by the mating of outer coupler external threads 619 with retaining cap internal threads 562. A pair of coaxial threaded holes 618 are defined in base section 606. Holes 618 are diametrically opposed and extend from outer annular surface 608 into bore 609. Holes 618 receive set screws 678.

Center section 620 has an outer annular surface 622 and a bore 624 defining an inner annular surface 626. An oval shaped slot 628 is defined in outer annular surface 622. Slot 628 extends perpendicularly part way into center section 620. An aperture 630 extends through the base of slot 628 into bore 624. A step 632 is defined at the junction of base section 606 and center section 620.

Top section 640 has an outer annular outer surface 642. A bore 646 extends proximally from the distal end of top section 640 to bore 624. Bore 646 is smaller in diameter than bore 624. Outer coupler 600 is further formed so that immediately forward of bore 624, two parallel opposed flats 648 project into the bore 646. In FIG. 30, the flats 648 are depicted as a pair of parallel lines. Top section 640 further includes an angled face 652 that extends from annular surface 642 and terminates in a distally oriented face 654 at distal end 604. An annular step 656 is defined at the junction of top section 640 and center section 620.

A pair of opposed angled arcuate slots 658 are formed on opposite sides of top section 640. Slots 658 are defined by opposed angled slot walls 660. Slots 658 begin at the outer surface 642 of top section 640, above step 656 and are angled in a distal direction inwardly toward bore 646. At the base of slot 658, an oval shaped hole 662 is defined that extends from slot 658 into bore 646.

With reference to FIGS. 6 and 11, a drill bit coupler or retainer assembly 1200 is illustrated. Drill bit retainer assembly 1200 includes outer coupler 600, release collar 670, coil spring 680, ring 690 and a pair of elongated rods or pins 694. Release collar 670 is generally cylindrical in shape and is formed from a single piece of metal. Release collar 670 has an outer annular surface 671 and a through bore 672. Bore 672 defines an inner annular surface 673. Release collar 670 has a distally directed partially cone shaped end 674 with an inwardly directed annular lip 677 and a proximal end 675. A threaded aperture 676 extends through release collar 670 spaced from proximal end 675. During assembly, a set screw 678 is seated in threaded aperture 676. Coil spring 680 has a distal end 682 and a proximal end 684. Ring 690 is circular in shape and has a through hole 692.

Drill bit retainer assembly 1200 is assembled with coil spring 680 mounted over outer annular surface 642 and spring proximal end 684 resting in contact with annular step 656. Ring 690 is placed over outer annular surface 642 and moved into contact with spring distal end 682. The outer coupler top section 640 extends through ring hole 692. Ring 690 is moved in a proximal direction compressing spring 680 and allowing pins 694 to be inserted into outer coupler slots 658. The release of ring 690 causes spring 680 to bias ring 690 and pins 694 to the distal ends of slots 658 adjacent hole 662. In this position, the center of pins 694 at least partially extend through holes 662 into outer coupler bore 646.

Release collar 670 is placed over ring 690 and spring 680 such that collar inner annular surface 673 is adjacent the spring 680. Spring distal end 682 rests in contact with the proximal directed surface of ring 690. The distal directed surface of ring 690 is located adjacent the distally directed faces of pins 690. Set screw 678 is seated in threaded aperture 676 with the set screw far end 679 extending into slot 628. Release collar 670 is now movably retained to outer coupler 600.

Release collar 670 can move in a longitudinal direction parallel to the axis of chuck assembly 300. Absent any other forces being applied to collar 670, spring 680 spring pushes ring 690 against the pins 694. The pins 690 are thus pushed into their most distal location in slots 658. When pins 690 are in this position, the pins hold the outer drill bit to the outer coupler 600. To move the lock assembly from the locked state to the load state, a user grasps the outer surface 671 and move release collar 670 in a proximal direction such that spring 680 is compressed. The travel of set screw end 679 within slot 628 limits the linear travel of release collar 670. The pins 694 can travel proximal in slots 658 away from the center axis of the outer coupler 600.

Input drive shaft 700 is illustrated with reference to FIGS. 32-36. Input drive shaft 700 is formed from a single piece of metal. Input drive shaft 700 is generally cylindrical in shape. Input drive shaft 700 has a distal end 702 and a proximal end 704. Input drive shaft 700 has three adjacent cylindrical sections, base section 706, center section 708 and shaft section 710. Center section 708 has a diameter that is less than the diameter of base section 706. Shaft section 710 has a diameter that is less than the diameter of center section 708.

Base section 706 has an outer annular surface 712 and a bore 714 defining an inner annular surface 716. The chuck assembly is formed so that there is a clearance of at least 0.05 mm between the outer diameter of outer coupler outer surface 608 and the surrounding input drive shaft annular surface 716. An inwardly directed lip 718 extends into bore 714 and faces in a distal direction. An annular proximal facing step 720 is defined at the junction of base section 706 and center section 708.

Center section 708 has an outer annular surface 722 and a bore 724 defining an inner annular surface 726. Bore 724 is contiguous with bore 714. A distal facing annular end wall 728 is located at the end of bore 724. An annular proximal facing step 730 is defined at the junction of shaft section 710 and center section 708.

A pair of opposed threaded apertures 732 extend through center section 708 slightly spaced from step 730 on opposite sides of bore 724. Threaded apertures 732 receive set screws 734 during assembly. Set screws 734 lock input drive shaft 700 to drive cap 402. Internal threads 736 are formed in inner annular surface 726. Internal threads 736 mate with drive cap external threads 408 such that drive cap 402 is affixed to input drive shaft 700.

An interior raised annular flange 738 extends from center section 708 in a distal direction into bore 714 and defines an annular slot 740. Annular slot 740 is defined between flange 738 and inner annular surface 716.

Elongated shaft section 710 has an outer annular surface 742 and a bore 744. Bore 744 extends through end wall 728 such that bore 744 is contiguous with bore 724. A pair of spaced annular grooves 746 and 748 are located in shaft section 710. Groove 746 is located toward the center of shaft section 710 and groove 748 is slightly spaced from proximal end 704. Grooves 746 and 748 are adapted to receive snap rings 750. Snap rings 750 retain input drive shaft 700 to end cap 310 (FIGS. 6A AND 6B). Shaft section 710 further has opposed rounded portions 752 and opposed flat portions 754 located toward proximal end 704. An annular proximal facing step 756 is defined at the junction of outer annular surface 742 and rounded portions 752 and flat portions 754.

With reference to FIGS. 6A, 24 and 35, A biasing component such as coil spring 950 is mounted between plunger 500 and input drive shaft 700. Coil spring 950 has a proximal end 952 and a distal end 954. Coil spring 950 is mounted in plunger bore 510 and surrounded by annular inner wall 512. Spring distal end 954 is adjacent to and in contact with plunger end wall 513. Proximal end 952 is adjacent to and in contact with input drive shaft end wall 728. Plunger 500 can move back and forth in a longitudinal direction within drive cap 402 such that coil spring 950 is compressed and at least partially decompressed. Spring 950 biases plunger 500 in a distal direction away from input drive shaft 700.

Figure 32:
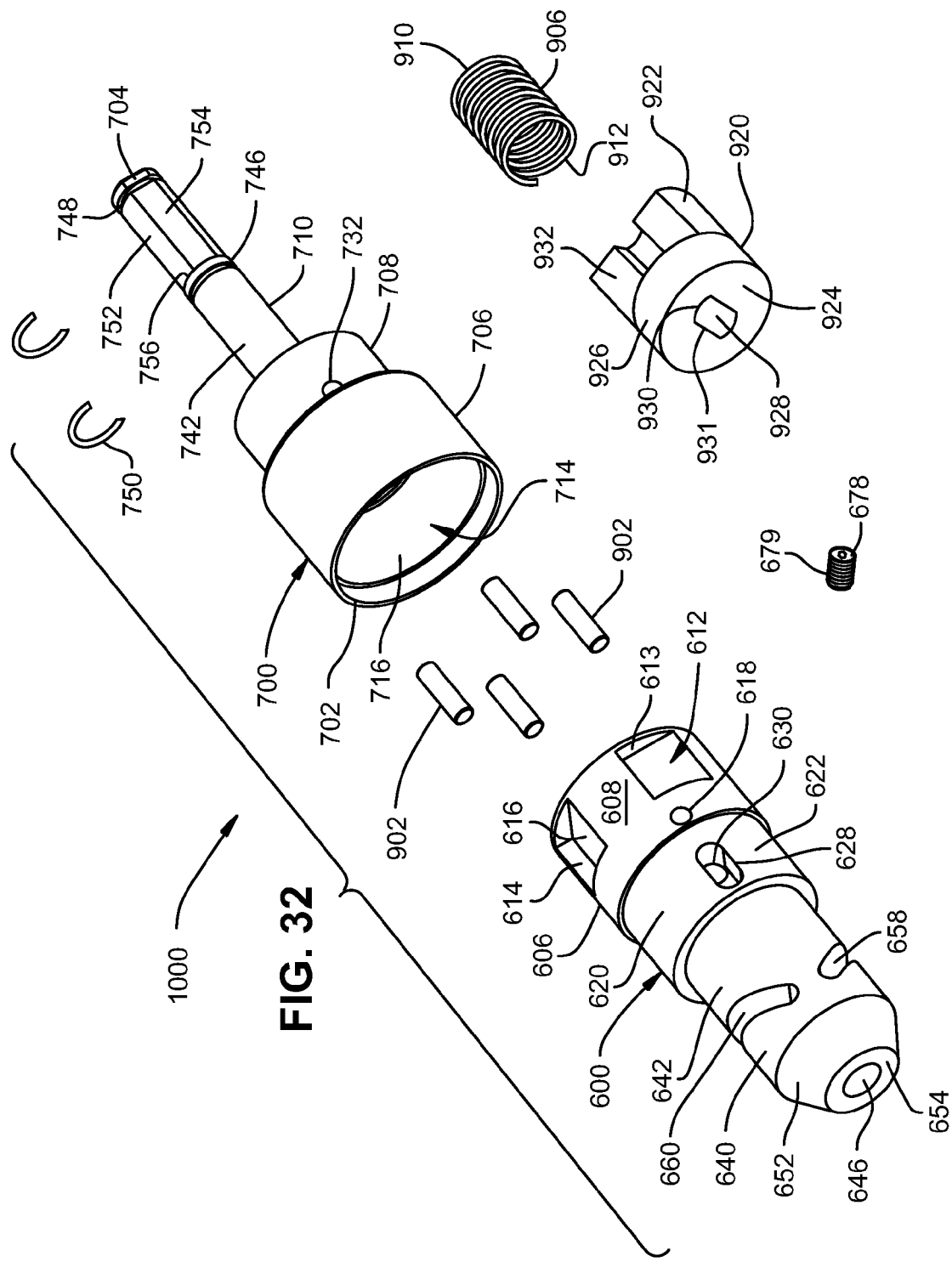
FIG. 32 is an exploded perspective view of the input drive shaft and outer coupler.

With reference to FIGS. 6, 11 and 32, shaft section 710 is inserted through bearing bores 332 such that outer annular surface 742 is supported for rotary motion by bearings 328 and 330. Step 730 is adjacent the distal directed face of bearing 328. A snap ring 750 is affixed in shaft groove 746. Snap ring 750 holds bearing 330 against inner rib 322. Coil spring 906 has a proximal end 910 and a distal end 912. Coil spring 910 surrounds shaft portions 752 and 754. Spring distal end 912 is seated against step 756 and spring proximal end 910 is seated against driving collar 920. Spring 906 is therefore retained between step 756 and driving collar 920.

Driving collar 920 is generally cylindrical in shape and has a proximal face 922 and a distal face 924. Driving collar 920 has an outer annular surface 926 and a bore 928 that defines a pair of opposed rounded inner surfaces 930 and a pair of opposed flat inner surfaces 931. A cutout 932 is located on proximal face 922 and extends from the outer annular surface 926 to the center of bore 928 and from proximal face 922 approximately half the length of collar 920.

Driving collar 920 is mounted over shaft section 710 such that shaft rounded portions 752 are adjacent collar rounded inner surfaces 930 and shaft flat portions 754 are adjacent collar flat inner surfaces 931. Distal face 924 faces the proximal side of bearing 330. Snap ring 750 is affixed in shaft groove 748 at shaft proximal end 704. Snap ring 750 holds driving collar 920 and spring 906 on shaft 710.

Rotary clutch assembly 1000 is described with reference to FIGS. 6A, 32-36 and 37. Rotary clutch assembly 1000 includes outer coupler 600, input drive shaft 700 and pins 902. Pins or needle bearings 902 are disposed in indentations 612 such that the ends of the pins are located adjacent opposite side walls 613 and one side of the pins 902 are adjacent to vertical walls 614. Input drive shaft base section 706 is slid over output coupler base section 608 such that base section 608 is disposed in bore 714 with inner annular surface 716 adjacent to outer annular surface 608. In this position, proximal end 602 of outer coupler 600 is located in annular slot 740 and the distal end 702 of outer coupler 700 is generally flush with the proximal side of apertures 618. Each pin 902 has a radius such that the sum of the distance from the center of plunger 500 to the center of a pin 902 plus the radius of the pin 902 is approximately 200 to 300 microns less diameter of input drive shaft annular surface 716 when the pin abuts outer coupler wall 614. In many preferred versions of the invention, the components must further be dimensioned so that when pin 902 seats against outer coupler end wall 614 and ramp 616, the outer surface of the pin projects beyond the outer diameter of outer coupler surface 608. In some versions of the invention pin 902 extends radially beyond the outer coupler 608 by a distance of at least 0.04 mm.

A small gap 904 (FIG. 37) separates outer coupler outer surface 608 from input drive shaft inner surface 716 and allows rotation between output coupler 600 and input drive shaft 700. Pins 902 are retained in indentations 612 between slot walls 613, 614, ramp 616 and input drive shaft inner annular surface 716.

Figure 37:
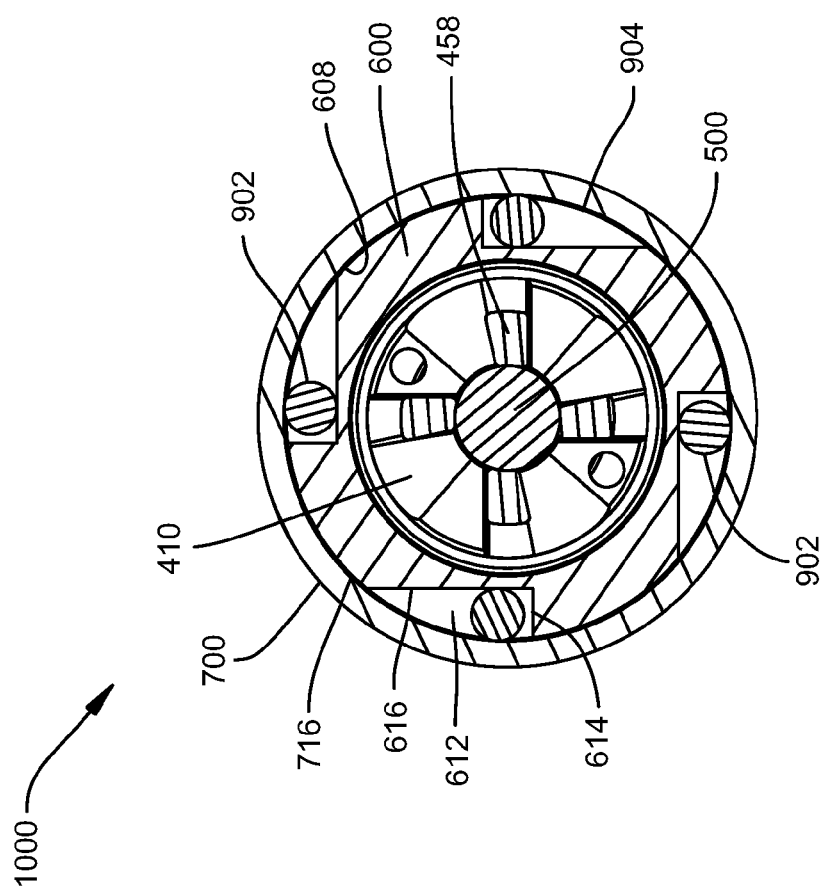
FIG. 37 is a cross-sectional view of the chuck assembly showing features of the rotary clutch taken along section line 37-37 of FIG. 9.

As seen in FIG. 37, when input drive shaft 700 is rotated in a forward or clockwise direction (as viewed from a proximal position), pins 902 move towards vertical wall 614. In this position, pins 902 are not in contact with outer coupler inner surface 716. Pins 902 are able to freely rotate in indentation 612. Therefore, input drive shaft 700 rotates without a like rotation of output coupler 600. When input drive shaft 700 is rotated in a reverse or counter clockwise direction, pins 902 move away from vertical wall 614 along ramp surface 616. In this position, pins 902 are jammed into contact between ramp surface 616 and inner surface 716 locking input drive shaft 700 and output coupler 600 together. Therefore, input drive shaft 700 rotates with a like rotation of output coupler 600. In the reverse drive position, input drive shaft 700 and output coupler 600 rotate in unison.

Rotary clutch assembly 1000 allows rotary motion of input shaft 700 in one direction to be transmitted to output coupler 600. Rotary motion of input shaft 700 in the counter clockwise direction is transmitted to output coupler 600. Rotary motion of input shaft 700 in the clockwise direction is not transmitted to output coupler 600.

IV. Assembly

Turning to FIGS. 6A, 14, 22, 25 and 35, the assembly sequence of chuck assembly 300 will now be described. Initially, plunger 500 is inserted through drive cap 402 bore 405 such that plunger head 506 is slip fit into drive cap bore 405 with drive cap inner wall 404 adjacent plunger outer surface 507 and plunger step 508 adjacent the inner end wall 415 of plate 410. Plunger head 506 can move slightly in an axial direction within bore 405. Spring 950 is inserted into plunger bore 510.

Next, the combination of the drive cap 402, plunger 500 and spring 950 are mounted to input drive shaft 700. The proximal end 407 of drive cap 402 and plunger proximal end 502 are placed in input drive shaft bore 724 and rotated such that internal threads 736 mate with drive cap external threads 408. A tool is inserted into bores 424 in order to rotate drive cap 402 during assembly. A fastener 734 such as a set screw is screwed into threaded aperture 732 until the end of set screw 734 jams against threads 408. Alternatively, fastener 734 can be replaced by an adhesive compound disposed on threads 408 and 736. Spring 950 is retained between input drive shaft end wall 728 and plunger 500. Drive cap 402 is now affixed to input drive shaft 700.

Figure 18:
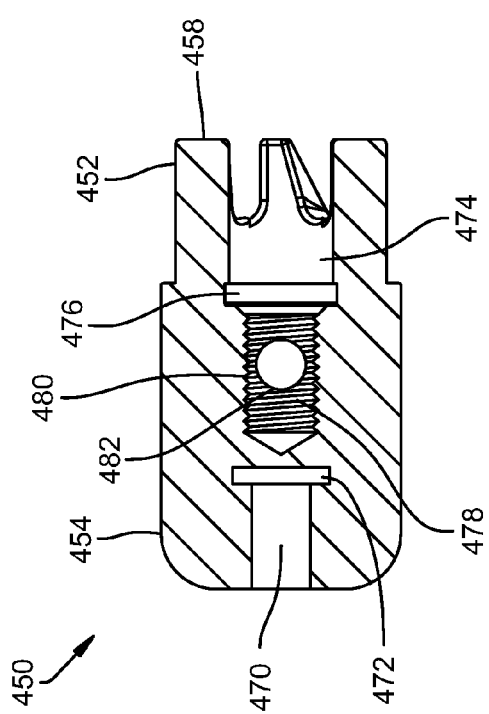
FIG. 18 is a cross-sectional view of the inner coupler.

With additional reference to FIGS. 18 and 25, retaining cap 550 is placed over inner coupler 450 such that legs 458 extend through bore 564 and slots 572. Inner coupler proximal section 452 is adjacent to inner annular wall 560. Inner coupler 450 and retaining cap 550 are placed onto plunger 500. Plunger distal stem section 518 is seated into inner coupler bore 478. The inner coupler 450 and retaining cap 550 are rotated with respect to each other. Inner coupler threads 480 mate with distal stem section threads 524 such that plunger 500 and inner coupler 450 are connected. A fastener 484 such as set screw 484 is rotated along threaded bore 482 until the end of set screw 484 jams into distal stem section threads 524. Set screw 484 locks inner coupler 450 to plunger 500. Alternatively, fastener 484 can be replaced by an adhesive compound disposed on threads 480 and 524.

With additional reference to FIG. 32, pins 902 are placed into indentations 612. The proximally directed bore 609 of outer coupler 600 is placed over the distally directed end face 468 of inner coupler 450, retaining cap 550 and driving cap 402. Output coupler 600 is moved in an axial proximal direction with output coupler base section 606 moving into input shaft bore 714. Output coupler 600 is rotated relative to retaining cap 550 such that outer coupler internal threads 619 mate with retaining cap external threads 562. Input coupler distal section 454 is disposed in output coupler bore 624. A fastener such as set screws 621 are rotated along threaded bores 618 until the end of set screws 621 jam into retaining cap threads 562. Set screws 621 lock outer coupler 600 to retaining cap 550. Output coupler 600 is now connected to input drive shaft 700. Alternatively, fastener 621 can be replaced by an adhesive compound disposed on threads 562 and 619.

It is noted that outer coupler 600 can move slightly in an axial direction relative to input drive shaft 700. The axial motion is parallel to the axis of drill bit assembly 200. Output coupler 600 can move in a proximal direction until drive cap faces 422 abut retaining cap ribs 570. In this position, while drive cap 402 may contact retaining cap 550, no rotary torque is transferred from drive cap 402 to retaining cap 550.

Drill bit retainer assembly 1200 is next mounted to chuck assembly 300. Coil spring 680 is mounted over outer annular surface 642 with spring proximal end 684 resting in contact with annular step 656. Ring 690 is placed over outer annular surface 642 and moved into contact with spring distal end 682. The outer coupler top section 640 extends through ring hole 692. Ring 690 is moved in a proximal direction compressing spring 680 and allowing pins 694 to be inserted into outer coupler slots 658. The release of ring 690 causes spring 680 to bias ring 690 and pins 694 to the ends of slots 658 adjacent hole 662. In this position, the center of pins 694 partially extend into holes 662.

Release collar 670 is placed over ring 690 and spring 680 such that collar inner annular surface 673 is adjacent the spring 680. Spring distal end 682 rests in contact with the proximal directed surface of ring 690. The distal directed surface of ring 690 is in contact with the proximally directed faces of pins 692. Set screw 678 is seated in threaded aperture 676 with the set screw far end 679 extending into slot 628. The release collar 670 is now movably retained to the outer coupler 600.

The release collar 670 can move in a longitudinal direction parallel to the axis of chuck assembly 300. A user can grasp the outer surface 671 and move release collar 670 in a proximal direction such that spring 680 is compressed. The travel of set screw end 679 within slot 628 limits the linear travel of release collar 670. Release collar 670 can only move along with set screw 678 between the proximal and distal ends of slot 628. When the user lets go of release collar 670, spring 680 biases the release collar to move in a distal direction until set screw end 679 contacts the distal end of slot 628. In this position, coil spring 680 is at least partially compressed.

The bearings 328 and 330 are seated in end cap 310. The input drive shaft section 710 is inserted through bearing bores 332 such that outer annular surface 742 is supported for rotary motion by bearings 328 and 330. Step 730 is adjacent the distal directed face of bearing 328. A snap ring 750 is affixed in shaft groove 746. Snap ring 750 holds bearing 330 against inner rib 322. Coil spring 906 is placed over and surrounds shaft portions 752 and 754. Driving collar 920 is placed over and surrounds shaft portions 752 and 754 with shaft portions 752 and 754 extending through bore 928. Driving collar 920 is moved in an axial distal direction compressing spring 906. Snap ring 750 is affixed in shaft groove 748 at shaft proximal end 704. Snap ring 750 holds driving collar 920 and spring 906 on shaft 710.

To fit drill bit assembly 200, the surgical personnel insert the assembly into output coupler 600. Initially, the drill bit annular flange 266 abuts pins 694. The manual force used to push the drill bit assembly proximally is sufficient to overcome the force spring 680 imposes on the pins 694 so as to hold the pins in the distal ends of slots 658. As a result of the continued proximal displacement of the drill bit assembly, pins 694 ride up over the outer surface of outer drill bit assembly annular flange 262. Drill bit assembly is then rotated until the flats of drive head 210 are parallel to the flats forming coupler bore 470, outer drill bit flats 264 are aligned with the outer coupler flats 648 and the outer drill bit grooves 268 are aligned outer coupler slots 658.

Drill bit assembly 200 is then pressed proximally until the proximal end of outer drill bit 250 and flat sections 264 are seated against outer coupler flats 648. Flange 262 is seated in the complementary output coupler bore 646. Flat sections 264 cause flange 262 to be rotationally aligned such that outer bit grooves 268 are in registration with the outer coupler holes 662 located at the bases of slots 658. When the drill bit assembly 200 is so positioned, the force of spring 680 imposes on pins 694 is sufficient to push the pins 694 into grooves 268. The seating of pins 694 in grooves 268 releasably holds the drill assembly 200 axially within the chuck.

V. Operation

The rotary surgical drill 100 is used at a surgical site by a medical practitioner. The practitioner grasps handle 104 and directs the drill bit cutting flutes 208 and 258 to the surgical site. Drill bit assembly 200 is used to drill one or more bores into a bone.

Initially, the drill bits 202 and 250 are not subjected to any axial loading. Pin 270 is positioned in a distal position within slot 266 such that inner bit flutes 208 extend slightly beyond outer bit flutes 258. Axial loading is defined as a force acting along the same axis as the longitudinal axis of drill bit assembly 200.

Figure 38:
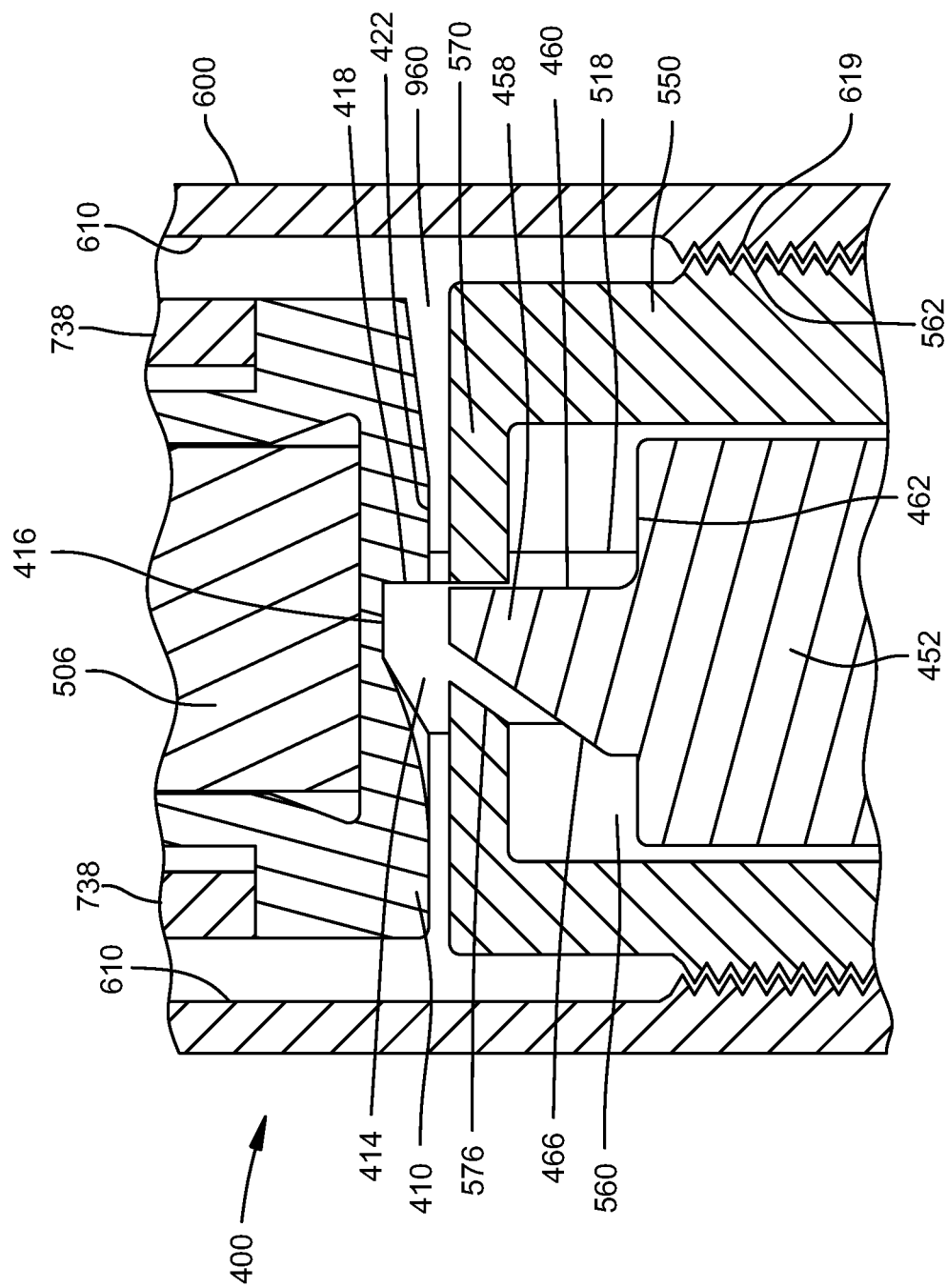
FIG. 38 is a cross-sectional view of the linear clutch assembly showing the relative orientation of the components when the inner coupler is in an initial disengaged position.

The force spring 950 imposes against the plunger 500 urges the plunger and the connected inner coupler 450, distally forward. Plunger 500 moves distally forward until plunger step 508 contacts drive cap end wall 415. This displacement of the inner coupler 450 away from the drive cap 402 is sufficient to result in displacement of the inner coupler legs 458 away from end plate 410. In this position, a gap 960, as shown in FIG. 38, is formed between driving cap end plate 410, retaining cap ribs 570 and inner coupler legs 458. As a consequence of the spacing of the inner coupler legs 458 away from the drive cap 402, the drive cap does not transfer any rotational moment it has to the inner coupler 450.

The practitioner readies the drill 100 for operation by positioning the handpiece 102 so the inner bit 202 is positioned against the bone where the bore is to be formed. The resistance of the bone prevents further forward movement of the inner bit 202 and the inner coupler 450. The continued force the practitioner applies to the handpiece overcomes the force imposed by the spring 950 in holding the drive cap 405 and inner coupler 450 apart from each other. The practitioner moves handpiece 102 distally forward so that the drive cap 402 moves against the inner coupler legs 458.

Figure 39:
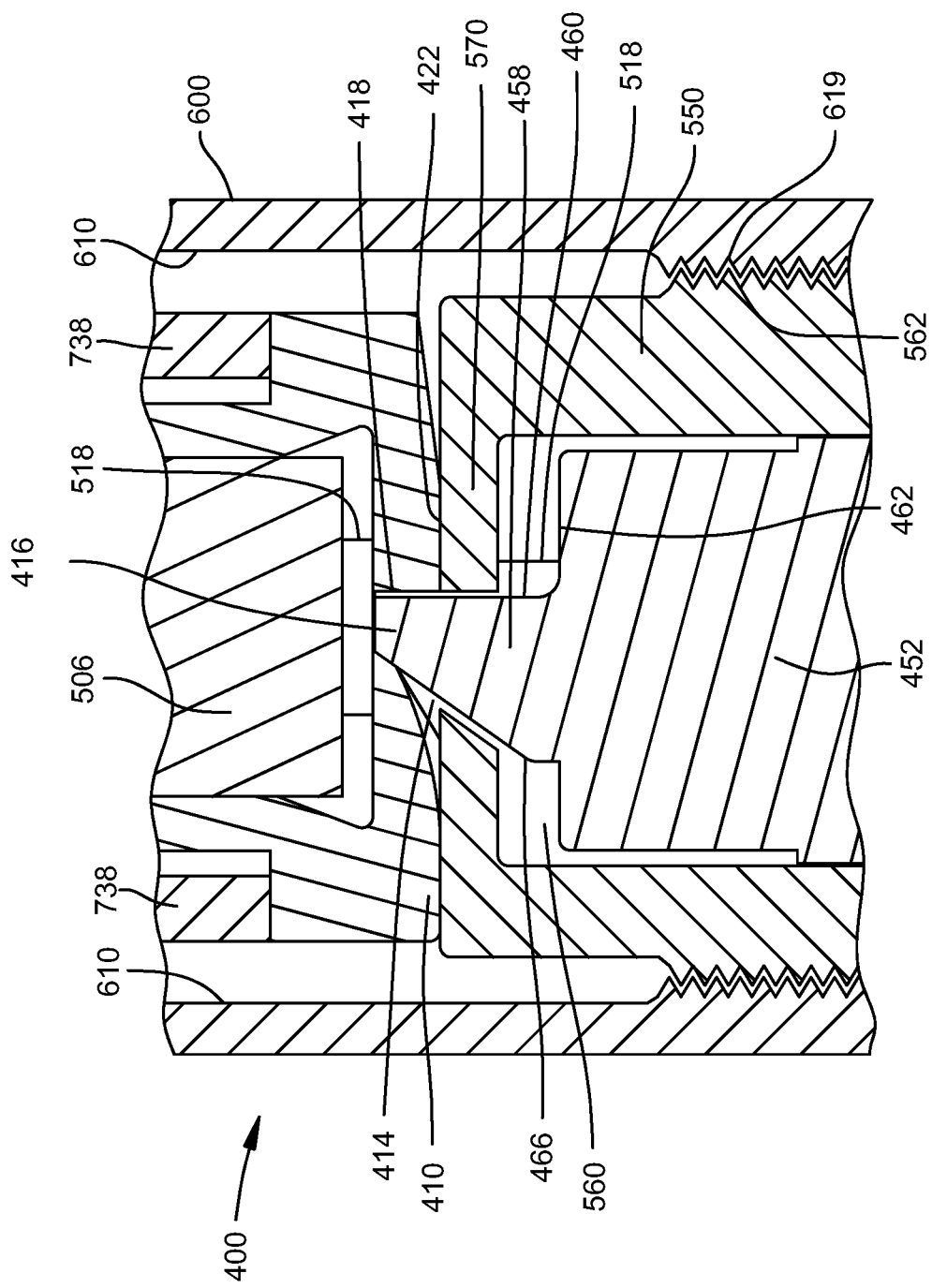
FIG. 39 is a cross-sectional view of the linear clutch assembly showing the relative orientation of the components when the inner drill bit is axially loaded and the inner coupler is engaged with the drive cap.

If the inner coupler legs 458 are aligned with the drive cap notches 414, the drive cap 402 seats against the couple legs 458 shown in FIG. 39. When the drive cap 402 and inner coupler are so positioned, the inner coupler can be considered to be engaged with the drive cap.

More typically, one of the outer surfaces of the drive cap seat against the inner coupler legs 458. When this event occurs, the drive cap 402 and inner coupler are not engaged. When the chuck 300 is in this state, as a consequence of the initial forward rotation of the drive cap 402, and the forward force imposed on the cap, the cap rotates so that notches 414 go into registration with the coupler legs 458. Specifically, as the drive cap rotates and is pushed forward, the cap ramps 420 rotate over the static coupler legs 458. This motion occurs until the legs 458 seat in the cap notches 414. This continues until the cap base surfaces 416 press against the surfaces 464 of coupler legs 458. The inner coupler 450 is thus considered to be engaged with the drive cap 402. Once the coupler legs 458 are so positioned the continued rotation of the drive cap 402 results in the abutment of cap wall surfaces 418 against the coupler leg surfaces 460. This is the cap-against-coupler contact that transfers the rotational moment of the cap 402 to the inner coupler 450.

Further forward rotation of the drive cap transfers the rotational moment applied to the cap to the inner coupler which transfers the moment to the inner drill bit 202. The initial rotation of inner drill bit 202 results in the formation of a small pilot bore in the bone.

A second effect of the rotation of inner coupler is that the coupler ramp surfaces 466 are pushed against the adjacent ramp surfaces 576 integral with retaining cap 550. This ramp surface 466-against-ram surface 576 abutment causes the retaining cap 550 to rotate with the inner coupler 400. Since the end cap is held fast to the outer coupler 600, the outer coupler engages in a like rotation. The rotation of the outer coupler causes a like rotation of the outer drill bit 250.

As a result of the forward force the practitioner applies to the handpiece 102 the drive cap 402 presses against the distally facing surface of retaining cap 550, this contact is not shown in FIG. 39. However, owing to the geometry of the outer surfaces of caps 402 and 550, this contact does not result in the transfer of torque from drive cap 402 to retaining cap 550. The above described ramp surface 466-against-ramp surface 576 abutment is the engagement that causes the outer coupler to rotate the outer drill bit 250. The pressing of drive cap 402 against retaining cap 550 is transferred by the outer coupler 600 to the outer drill bit 250. This is the axial force that pushes the outer drill bit 250 into the bone. This combination of axial loading and torque causes the flutes of the outer drill bit to cut the bone.

When the input drive shaft 700 rotates in the forward direction, the shaft would, in FIG. 37, appear to rotate clockwise direction. This rotation of the shaft results in the rolling of the pins 902 towards vertical walls 614. Owing to the dimensioning of the components, pins 902 are not compressed between the input drive shaft annular surface 716 and one of the outer surfaces of the outer coupler 600. Pins 902 in this state do not function as components that transfer the rotational moment of the input drive shaft to the outer coupler 600.

During the initial process of forming the bore in the bone, the outer drill flutes 258 may only abut the bone. Since the outer drill flutes 258 are not pressed against the bone, even though they are rotating, in this stage of the process, they do not cut the bone.

As the process of the bore being formed in the bone by the inner drill bit 202 continues, the outer bit flutes 258 contact the bone and are subject to axial loading. The rotating outer drill bit flutes 258 are forced against bone. The action of flutes 258 forms a counter bore around the bore formed by the inner drill flutes 208.

From FIG. 39, it can further be observed that, as a consequence of the dimensioning of the components, when the inner coupler legs 458 seat in end plate notches 414, the width of the slice section of each coupler leg seated in a cap slot 572 is less than the width the cap slot. Therefore, there is sufficient clearance in slots 574 for the legs 458 to fully seat in the end plate notches 414 and for there to be a small play in between the legs 458 and surrounding retaining cap ribs 570. When the chuck is driven in forward direction, as described above, each coupler leg ramp surface 466 abuts the adjacent retaining cap ramp surface 576. Accordingly, during forward rotation of the inner coupler, there is an angular separation between each coupler leg vertical surface 460 and the adjacent surface of the retaining cap. This angular separation is typically at least 0.5° and in some versions of the invention, at least 2°. When inner coupler legs 458 are extend away from notches 414, surfaces 466 and 576 allow between 2 to 10 degrees of rotation to occur between inner drill bit 202 and outer drill bit 250. The maximum rotation between the inner and outer drill bits is limited by the geometrical dimensions of pin 270 in slot 266 of the drill bit assembly.

Eventually, the inner drill flutes 208 cut through the bone in which the bore is being formed. Since the outer drill flutes 258 are proximally rearward of the inner drill flutes 208, the outer drill flutes 258 remain embedded in the bone. At this time, the axial resistive and torque loads the bone places on the inner drill bit 202 essentially fall to zero. The inner drill bit 202 still receives the torque transmitted by the drive cap 402 to the legs 458. At this time, the bone still places a resistance on the rotation of the outer drill bit 258. Further, at this time, the full axial load supplied by the practitioner is fully transferred through the outer drill bit 258 to the bone. Owing to this difference in axial loading, the abutment of the coupler ramp surfaces 466 against the retaining cap ramp surfaces 576 drives the inner coupler distally forward, away from drive cap 402. The force of spring 950 against the inner plunger 500 also pushes inner coupler 450 away from drive cap 402.

The forward, distal displacement of the inner coupler 450 away from the drive cap 402 returns the inner coupler to the disengaged position shown in FIG. 38 in which the inner coupler legs 458 are positioned forward of the endplate notches 414. At this point, the inner drill bit 202 no longer receives any rotational motion or torque from the input drive shaft 700 and drive cap 402. Inner coupler thus stops transmitting rotary motion and torque through retaining cap 550 to the outer coupler 600. Owing to the resistance the bone places on the outer drill bit flutes 258 in opposition to their rotation, the outer bit also stops rotating. The axial thrust of the surgeon is support by the outer drill bit resting on the counterbore formed by the outer drill bit. This blocks further penetration of the inner drill bit 202 into the patient. Moreover, after the inner drill bit 202 cuts through the bone, drill bit assembly 200 stops rotating. This substantially eliminates the cutting of tissue adjacent where the inner bit 202 protrudes through the bone.

Spring 950 now holds the inner coupler 450 in the disengaged state.

The medical practitioner then retracts the drill bit assembly 200 from the bore. The practitioner can perform this process by actuating the handpiece 102 to cause the reverse rotation of the drill bit assembly 200.

The rotary drill is actuated in a reverse or counter clockwise rotation (as viewed from behind the handpiece) by the depression of trigger switch 108. Trigger switch 108 causes the handpiece motor rotate the input drive shaft 700 and drive cap 402 in a counter clockwise direction. Because linear clutch assembly 400 is disengaged, there is initially no rotation of drill bit assembly 200.

In FIG. 37, the reverse rotation of the drill assembly would appear as a counterclockwise rotation of the input drive shaft 700. Owing to centrifugal forces, at least one of the pins 902 contacts inner drive shaft surface 716. Owing to the frictional contact of the pin 902 with the surfaces 614 and 616 of the outer coupler 600, the pin does not rotate around the axis of the input drive shaft 700 at the same speed as the input drive shaft. This results in the wedging of the pin 902 between the outer coupler surface 616 and the input drive shaft annular surface 716. The remaining pins 902 likewise wedge between the outer coupler surface 616 and the input drive shaft 700. The interference fit of the pins 902 locks input drive shaft 700 and output coupler 600 together for simultaneous rotation.

One effect of the reverse rotation of the outer coupler 600 is that the outer coupler drives the outer drill bit 250 in a like reverse rotation.

A second effect of the reverse rotation of the outer coupler 600 is that simultaneous rotation of the retaining cap 550 results in the end cap ramp surfaces 576 abutting the adjacent ramp surfaces 466 integral with the inner coupler 450. This ramp surface-against-ram surface contact forces the inner coupler 450 into a like reverse orientation. The reverse rotation of the inner coupler 450 results in the like reverse rotation of the inner drill bit 202.

The simultaneous reverse rotation of the inner and outer drill bits substantially reduces the axial force the practitioner needs to apply to the handpiece in order to retract the drill assembly 200 from the bore.

Linear clutch 400 of the chuck of this invention makes it possible to after a drill bit penetrates the bone, stop the drill bit from rotating. The chuck assembly 300 of the present invention using rotary clutch 1000 allows a drill bit assembly forming a bone bore to be rotated in a reverse direction in order to remove the drill bit assembly from the bore.

After the medical practitioner has removed the drill bit assembly 200 from the bone bore, the depth gauge 274 can be used to measure the depth of the bore. This because, during the formation of the bone bore, because depth gauge 274 abuts the outer surface of the bone. The distal movement of the drill bit assembly 200 into the bone bore forces depth gauge 274 to slide along the outer circumference of the outer bit 250. The depth gauge 274 stops sliding along outer bit 250 when the inner bit penetrates the opposite side of the bone and linear clutch 400 is disengaged.

Consequently, when drill bit assembly 200 is removed from the bone bore, the depth gauge 274 is positioned along outer bit 250 such that the distance between the distal face of depth gauge 274 and the distal tip of drill bit flutes 208, 258 measures the depth of the bone bore. This depth can be read using a ruler. Markings on the outer surface of bit 250 may also be used to provide this measurement. Alternatively, the medical practitioner can place bone screws adjacent the depth gauge and visually select the bone screw that matches the depth of the bone bore. The presence of the depth gauge integral with the drill bit assembly 200 eliminates the need to after the bore is formed, employ a separate depth gauge to determine the depth of the bore.

FIGS. 40A-40D illustrate how the drill bit assembly 200 attached to the drill of this invention can be used to form a bore in a bone 1102 that has an outer cortical shell that surrounds an cancellous core. Cancellous bone is significantly less dense, more porous, then the surrounding cortical bone. In the Figures, these different section of the same bone 1102 are represented as an upper layer 1104 of cortical bone, a center located cancellous layer 1106 and a lower layer 1108 of cortical bone. The cortical layers 1104 and 1108 inner surfaces are the surfaces adjacent the cancellous layer 1106. The cortical layer outer surfaces are the surfaces spaced from the cancellous layers, the outer surfaces if the bone 1102. Also seen in FIGS. 40A-40D is the soft tissue layer 1114 adjacent the outer surface of the lower cortical layer 1108. This soft tissue can comprise, the muscles, neurological tissue, ligaments, blood vessels, body organ and the epidermal tissue (skin).

Figure 40:
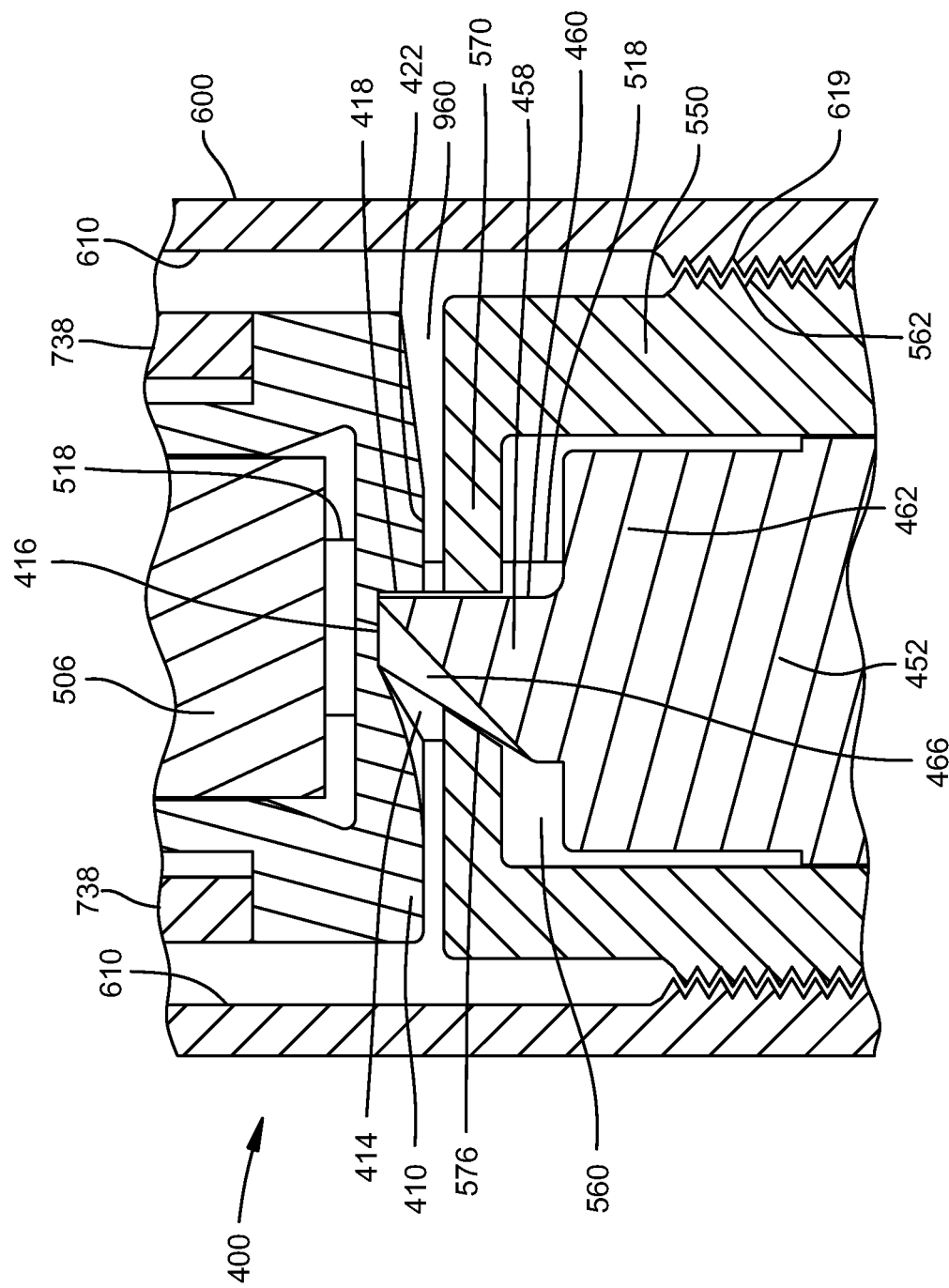
FIGS. 40A-40D are a sequence of cross sectional views that depict how the drill of this invention is employed to form a bore in section of bone that comprises layers of cortical and cancellous material.
Figure 40A:
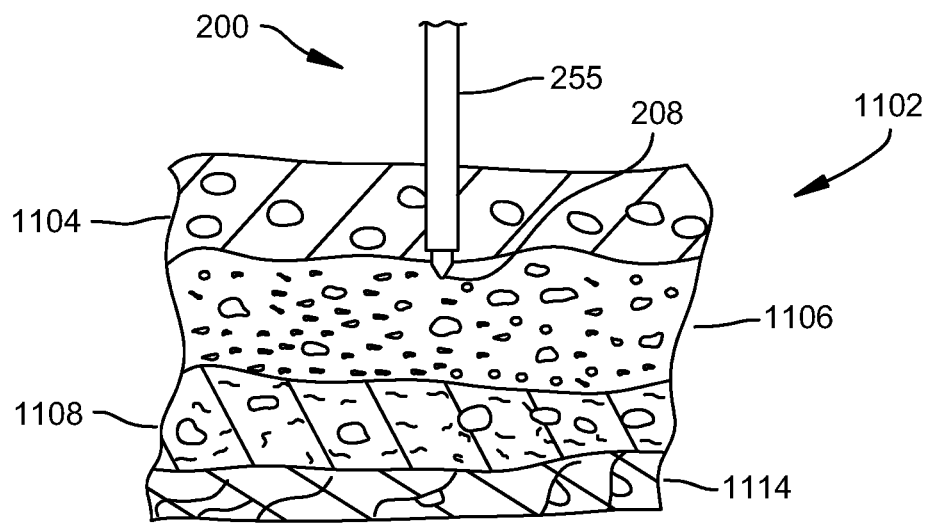

Using the drill of this invention, drill bit assembly 200 is advanced partially through the upper cortical layer 1104. In this step, the drill is driven in the forward direction. The chuck is placed in the engaged state of FIG. 39. Once the inner bit penetrates the inner surface of the upper cortical layer 1104, the axial forces imposed on the inner coupler 450 are opposed by more yielding lower density bone forming the cancellous layer 1106. These axial forces are sufficient to overcome the resistance of the cancellous layer tissue and drive the inner coupler and inner drill bit into the disengaged state. As depicted by FIG. 40A, this disengagement of the drill bit assembly 200 can occur even when the distal end of the outer bit 250 remains embedded in the upper cortical layer 1104.

Figure 40B:
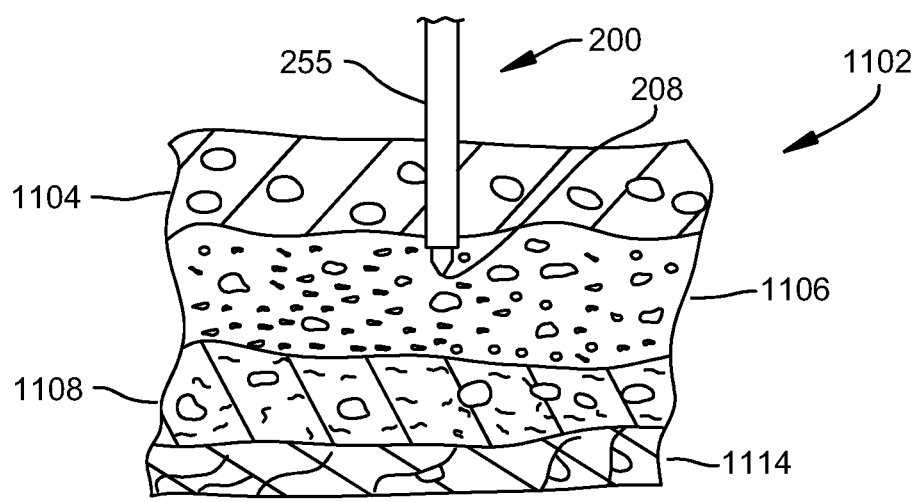

To now advance drill bit assembly 200, the drill can be driven in the reverse direction. Owing to the engagement of the outer coupler 600 with the input drive shaft 450, this results in the reverse rotation of the drill bits 202 and 250. The axial force the practitioner applies to the drill bit assembly, in combination with the torque the drill bit flutes 258 place on the cortical bone against which they are pressed, results in the cutting away of this bone. It should be appreciated that in these versions of the invention the cutting flutes of the drill assembly should be capable of bi-directional cutting. As represented by FIG. 40B, the drill bit is advanced until the outer drill bit 250 penetrates the inner surface of the cortical bone outer layer 1104. The drop in resistance the surgeon is exposed to upon the outer bit penetrating the upper cortical layer serves as a tactile feedback that the distal ends of the both the inner and outer drill bits 202 and 250, respectively, have entered the cancellous layer 1106. Chuck returns to the disengaged state of FIG. 38. Upon being exposed to this feedback, the surgeon may choose to deactivate the drill.

During the above step, the inner bit flutes 208 cut through cancellous bone tissue of layer 1106. As this is tissue that is to be removed to form the desired bore, this tissue removal is not the type of tissue remove the drill of this invention is intended to minimize.

The surgeon then advances the drill bit assembly 200 through the cancellous layer 1106. Owing to the relatively porous, less dense characteristics of the cancellous bone, this step may be performed by simply applying an axial force to press the drill bit forward. The bore formed by the bit assembly 200 in the upper cortical layer 1104 constrains the bit from movement away from the axis of this bore. Consequently the section of the bore formed in the cancellous layer 1106 is substantially coaxial with the bore formed in layer 1104.

Figure 40C:
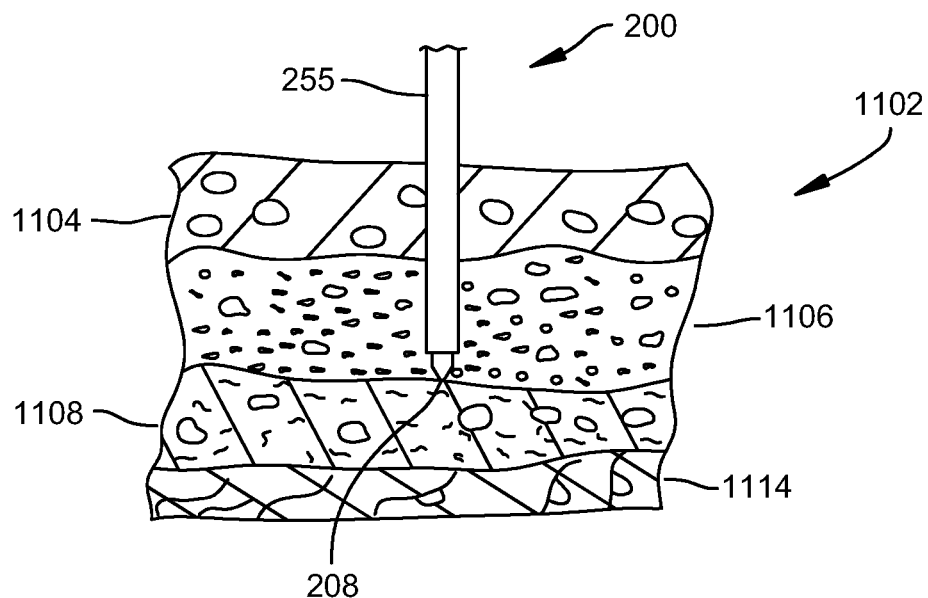

As depicted by FIG. 40C, bit assembly 200 is advanced through the cancellous layer 1106 until the inner bit flutes 208 abut the inner surface of the lower cortical layer 1108. The increased resistance the practitioner feels when the inner bit initially abuts the lower cortical layer 1108 functions as the feedback that the bit assembly is so positioned.

To advance the bit assembly 200 through the lower cortical layer 1108, the drill 100 is actuated to drive the inner coupler 450 in the forward direction. The chuck returns to the engaged state of FIG. 39. This results in the drill bits 202 and 250 being rotated in the forward direction against the lower cortical layer 1108 so as to form the section of the bore in this layer.

As mentioned above, in many versions of the invention, portions of the outer drill bit flutes 258 project radially beyond the bit shaft 255. Consequently, upon the formation of the bore in the upper cortical layer 1104, there is a small clearance between the bit shaft 255 and the surrounding portion of cortical layer that defines bore being formed. This means that, when the bit assembly is rotated to form the bore section in the lower cortical layer 1108, the dense bone of the upper cortical layer 1104 does not impose side load forces on the drill bit that slow the advancement of the drill bit.

Figure 40D:
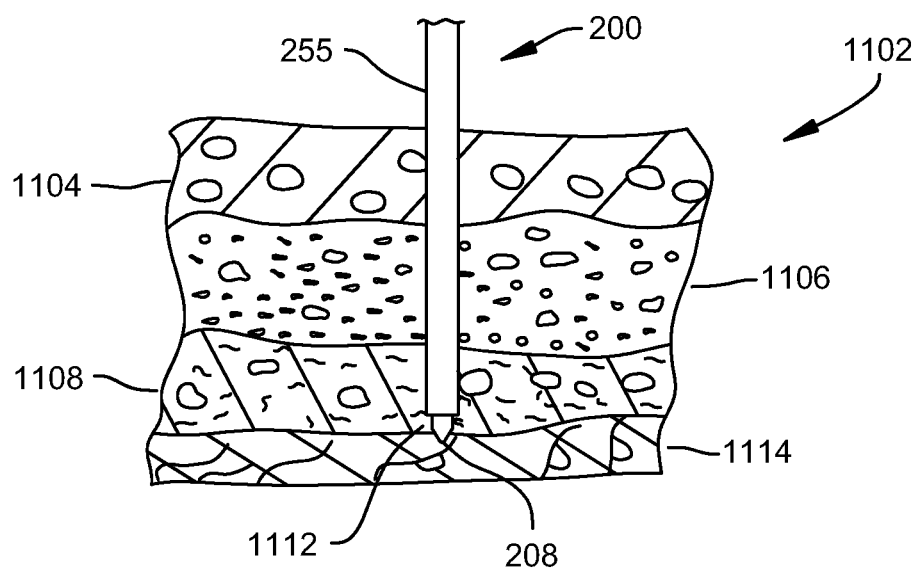

Bit assembly 200 is advanced through the lower cortical layer 1108 until, as seen in FIG. 40D, the inner drill bit 202 extends through the outer surface of layer 1108. When this event occurs, the distally directed forces imposed on the inner coupler 450 disengage the coupler 450 from the input drive shaft 700. Chuck 300 returns to the state as depicted in FIG. 38. This serves to rapidly terminate the rotation of the inner drill bit 202 before such rotation can significantly damage the tissue forming layer 1114.

Drill 100 is then driven in reverse to extract bit assembly 200 from the bore formed in bone 1102. (Not illustrated is the bore left after bit assembly 200 is extracted.)

As seen in FIG. 40D upon the disengagement of the bit assembly 200 with the drill 100, outer drill bit 250 may still be embedded in the lower cortical layer 1108. Upon extraction of the bit assembly 200 from the bone 1102, this may mean that an annular lip 1112 remains in place in the lower cortical layer 1108 adjacent the outer surface of the layer 1108. This lip 1112 projects into the bore left behind by the drilling action. This lip has a thickness of between 1 and 2 mm. Depending on the characteristics of the bone and the particular procedure, the lip may not even extend circumferentially around the bore.

VI. First Alternative Embodiment

Referring to FIGS. 41 and 42, an alternative chuck assembly 1500 of a drill of this invention is shown. Chuck assembly 1500 includes a cylindrical shaped housing 1510 with a through bore 1512. The housing 1510 has a head 1520 mounted within bore 1512. Head 1520 is connected to the output shaft of the handpiece 102 (FIG. 1) of this assembly. Internal to the housing 1510 within bore 1512 is a drum 1530. Drum 1530 is able to both rotate and move longitudinally within the housing 1510. A drill bit retainer assembly 1200 is coupled to the housing 1510.

Chuck 1500 is used with drill bit assembly 1538. Drill bit assembly 1538 includes tubular shaped outer bit 1540. An inner bit 1544 in the form of an elongated shaft extends through the longitudinally extending bore of the outer bit 1544 (outer bit bore not identified). and an inner bit 1544. Inner drill bit 1544 has a squared off proximal end 1542 that is seated in a squared off bore formed in drum 1530 (drum bore not identified). The inner bit 1544 extends a short distance forward of the distal end of the outer bit 1540. The exposed distal end of the inner bit 1544 is provided with cutting flutes.

Outer drill bit 1540 is formed with flutes 1541. Flutes 1541 are helical and that extend substantially the length of the bit. Outer drill bit 1540 is further formed so that there are two parallel opposed flats (not identified) at the most proximal end of the flute. A groove (not illustrated) extend inwardly from the surface of each flat. The grooves extend along axes that are coplanar and perpendicular to the longitudinal axis of the drill bit.

Drill bit retainer assembly 1200 includes two pins 1210 (one identified). Each pin 1210 seats in a bore in the below described outer coupler 1570. Theses bores are coaxial and extend along an axis perpendicular to the longitudinal axis of the outer coupler 1570. Each pin 1210 has a head dimensions to seat in one of the grooves formed integral with one of the flats of the outer drill bit 1544. Drill bit retainer assembly 1210 includes a shell 1214 that is disposed over outer coupler 1570. Shell 1214 is dimensioned to move longitudinally over the outer coupler. Shell 1214 has an inner annular surface 1216 that is space a small distance, approximately 0.5 mm away from the portion of the coupler 1570 in which pins 1202 are seated. Forward of surface 1216, shell 1214 has a groove 1218 that extends radially outwardly from the surface. Shell 1214 includes an annular skirt 1220 that extends proximally away from the portion of shell that defines surface 1216. Skirt 1220 is dimensioned to be spaced away from the underlying outer coupler 1570.

A spring 1222 extends forward from the proximally directed face of housing 1510. Spring 1222 extends into the annular space between skirt 1220 and outer coupler 1570. Spring 1222 presses against the annular step of shell 1214 that is located immediately inward of the inner annular surface of skirt 1220. Spring 1222 exerts sufficient force of shell 1214 to position the shell so that surfaces 1216 are normally disposed against the outer coupler bores in which pins 1210 are seated. Thus the spring 1222 normally holds the shell 1214 in the locked state in which the shell prevents the outward movement of the pins 1210. The pins 1210 seated in the grooves integral with the outer drill bit thus hold the outer drill bit to the outer coupler. The force the spring 1222 imposes on the shell 1214 can be overcome by manual force. Thus, to move the chuck to the release state, the shell is pushed rearwardly. This places shell groove 1218 in registration with the pins 1210. The pins 1210 are then free to retract radially outwardly. This outward radial movement of the pins makes it possible to remove and replace the outer drill bit 1540.

The housing head 1520 and drum 1530 are formed with complementary teeth represented by line 1550. These teeth, when engaged hold the drum 1530 to the head 1520 so that the drum 1530 rotates in unison with the housing 1510. A compliant biasing component 1560, such as a spring, normally biases the drum 1530 so that the head 1520 and drum 1530 are not engaged.

Chuck 1500 includes an outer coupler 1570. The outer coupler 1570 has a based disposed in housing bore 1512. The coupler 1570 has a wide diameter base, not identified. The base has an open such that drum 1520 can seat in the base. The outer surface of the outer coupler base is formed with indentations similar to indentations 612 of outer coupler 600. A pin 902, (one depicted but not identified) seats in each recess.

A first bearing, bearing 1522, provides a low friction interface between an outer portion of the outer coupler base and head 1520. A second bearing, bearing 1524 provides a low friction interface between the outer coupler 1570 and housing 1510. Bearing 1524 is seated around the stepped surface between the outer coupler base and the portion of the outer coupler that extends distally forward of the base.

The inner cylindrical surface of the outer coupler base and the outer surface of drum 1530 are formed with complementary teeth. In FIG. 42 these teeth are called out as line 1580. The engagement of the teeth ensures that to allow the drum 1530 to move longitudinally within the outer coupler 1570 while ensuring that the drum and outer coupler rotate in unison.

Head 1520, drum 1530 and spring 1560 collectively form a linear clutch 1600. Normally, spring 1560 holds the drum in a disengaged state relative to the head 1520. Chuck 1500 is used by pressing the tip 1544 of the drill bit against the bone in which the bore is to be formed. The resistance of the bone overcomes the spring force that holds the drum 1530 away from the housing head 1520. The linear clutch drum 1530 thus engages with the linear clutch housing head 1520. When the chuck assembly 1500 is in this position, the linear clutch 1600 is engaged and the chuck assembly is in the first engaged state. When the chuck assembly is in this state, the linear clutch 1600 transfers the forward and any reverse moment output by the handpiece 102 to the drum 1530 and, by extension to the drill bit 1540. The drill bit assembly forms a bore hole in the bone.

Upon the drill bit 1540 fully penetrating the bone, the bone ceases to offer a resistance in opposition to the disengaging force provided by the biasing component 1560. Spring 1560 urges the drum 1530 away from the housing head 1520. This disengagement of the drum 1530 from the housing head 1520 and complementary features 1550 stops the transfer of rotation power to the drill bit 1540. The distal tip 1544 of the drill bit therefore does not rotate against the soft tissue against which the drill bit is pressed.

Housing 1510, pins 902, outer coupler 1570, drum 1530 collectively form a rotary clutch 1650. Clutch 1650 operates in the same general means in which the rotary clutch of the first embodiment of the invention operates. When housing is rotated in one direction, pins 902 are not wedged between the housing and the outer coupler. The torque output by the housing 1510 is therefore not transferred to outer coupler 1570. When the outer housing rotates in the opposed direction, the pins wedge between the housing and the outer coupler. This results in the transfer of torque to the outer coupler and by extension the drill bit assembly.

Consequently, after the drill bit 1540 has formed a bore and penetrated the bone, the medical practitioner can reverse rotate the drill bit 1540 in order to, with minimal pulling force, withdraw the drill bit from the bone bore.

VII. Second Alternative Embodiment

Figure 43:
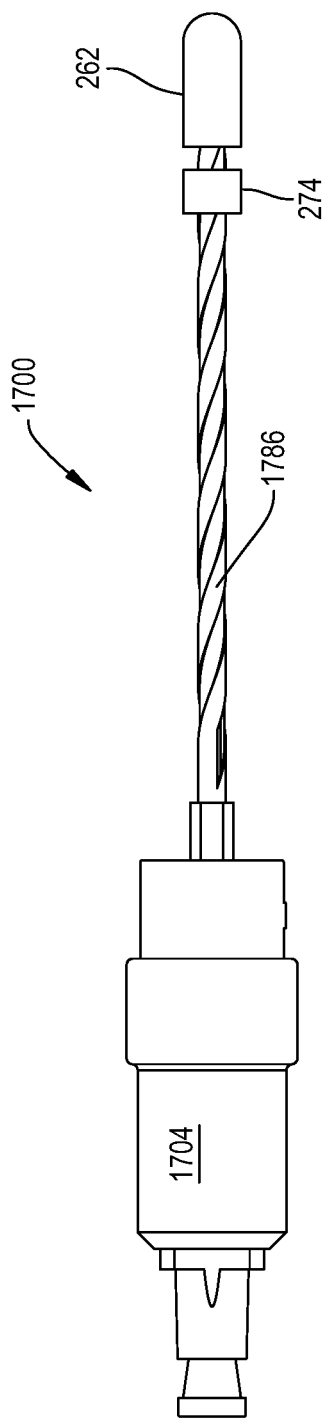
FIG. 43 is plan view of an alternative surgical drill of this invention.
Figure 44:
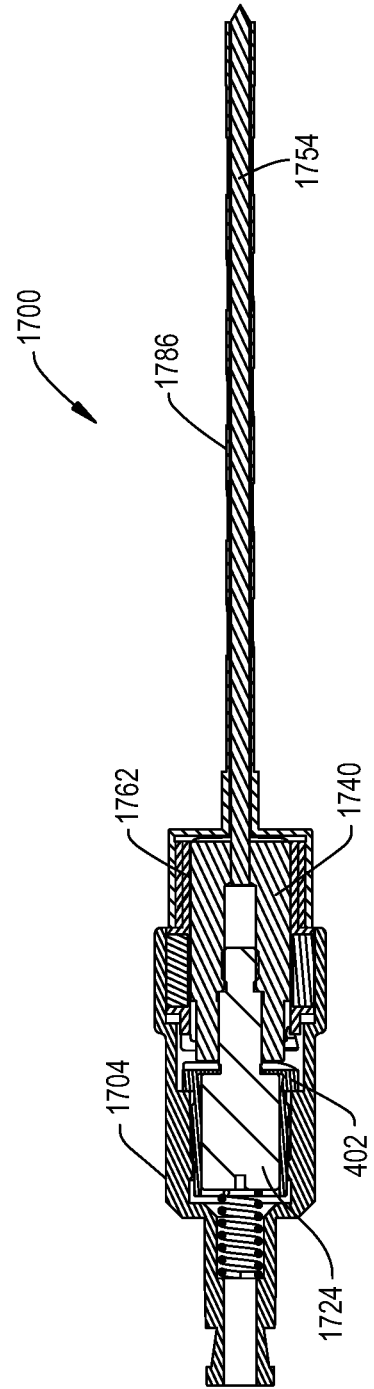
FIG. 44 is a cross sectional view of the surgical drill of FIG. 43.

FIGS. 43 and 44 illustrate an alternative drill assembly 1700 of this invention. Drill assembly 1700 is designed to connect to a handpiece that has a conventional chuck. Drill assembly 1700 includes an input drive shaft 1704, an inner coupler 1740 and an outer coupler 1762. An inner drill bit 1754 extends distally forward from the inner coupler 1740. An outer drill bit 1786 is disposed over the inner drill bit. The outer drill bit 1786 is mounted to rotate with the outer coupler 1762. Shown only in FIG. 43 is the cap 272 disposed over the distal ends of the inner and outer drill bits 1754 and 1786, respectively. Also seen only in FIG. 54 is the depth gauge 274 that is disposed over the outer drill bit 1786.

Figure 48:
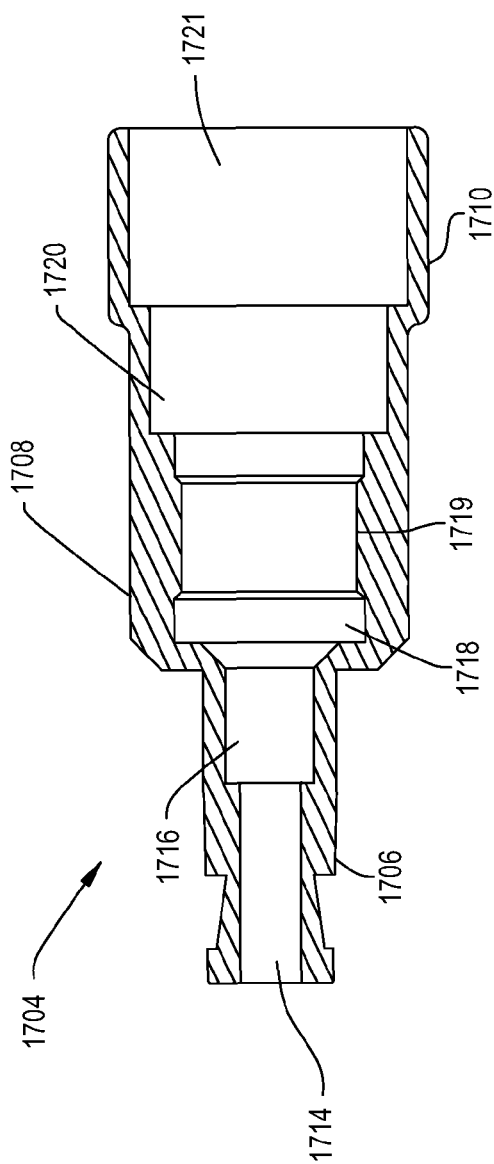
FIG. 48 is a cross sectional view of the input drive shaft of the surgical drill of FIG. 43.

As seen in FIG. 48, the input drive shaft 1704 is a single piece component. Shaft 1704 has a stem 1706. The stem 1706 is formed with geometric features that facilitate the relaeasble coupling of the stem to the chuck of the handpiece used to drive the assembly. The illustrated stem 1706 has features that facilitate the coupling of the stem 1706 to what is known as a Trinkle chuck. As these features are specific to the chuck for which drill assembly 1700 is designed, these features are not further discussed. A body 1708 is located forward of stem 1706. Body 1708 is cylindrical in shape and has an outer diameter greater than that of the stem 1706. A head 1710, located forward of the body 1708, is the most distal portion of the input drive shaft 1702. The head 1710, like body 1708 is generally cylindrical in shape. Head 1710 has an outer diameter that is greater than that of the body 1708.

A number of contiguous bores extend axially through the input drive shaft 1704. Two linearly aligned bores, boars 1714 and 1716, are disposed in the stem 1706. A first one of the bores, bores 1714, extends forward from the proximal end of the stem 1706, which is the proximal end of the shaft 102. Bore 1714 opens into bore 1716. Bore 1716 has a diameter greater than that of bore 1704. The distal end of bore 1716 is contiguous with a bore 1718. The input drive shaft 1704 is formed so that bore 1718 is disposed in shaft body 1708. Bore 1718 is greater in diameter than bore 1716. Shaft 1704 is formed so that the inner wall of the shaft that defines bore 1718 is formed with threading 1719. The bore 1718 extends to a bore 1720 also formed in the shaft body formed in the shaft head 1710. Bore 1720 has a diameter that is larger than the diameter of bore 1718. The bore 1720 opens into a bore 1721 formed in the head 1710 of the shaft 1704. The bore 1721 has a diameter larger than that of bore 1720. Bores 1714, 1716, 1718, 1720 and 1721 are coaxial. The distal end of bore 1721 forms the distal end opening into the input drive shaft 1704.

A plunger 1724 is slidably disposed in shaft bores 1718 and 1720. Plunger 1724 is generally similar to the previously disclosed plunger 500. As identified in FIG. 45, plunger 1724 has a cylindrical head 1726. Head 1726 has a diameter less than that of shaft bore 1718. A cylindrical stem proximal section 1728 extends distally forward from the distally directed face of head 1726. Stem proximal section 1728 has a diameter less than that of head 1726. A stem distal section 1730 is integral with and located forward of the stem proximal section 1728. Stem distal section 1730 is cylindrical in shape and has an outer diameter generally equal to the outer diameter of the stem proximal section. Not illustrated is the threading around the outer cylindrical surface of the stem distal section 1730.

Previously described drive cap 402 is secured in input shaft bore 1718. It should thus be appreciated that the cap 402 is threaded in bore 1718 so that the cap rotates in unison with the shaft 1704. The proximally facing annular surface of cap end plate 410 seats against the circular step within the shaft 1704 that defines the separation between bore 1718 and 1720. Plunger stem proximal section 1728 extends through cap opening 412. The components of drill 1700 are assembled so that plunger head 1726 has a limited amount of longitudinal movement within shaft bores 1718 and 1720.

A spring 1732 extends through shaft bore 1716 and abuts the proximally directed end of plunger 1724. The proximal end of spring 1732 is seated on the circular step between bores 1714 and 1716 internal to the input drive shaft 1704. The distal end of the spring 1732 presses against the proximally directed face of plunger head 1726. Spring 1732 thus pushes the plunger 1724 distally forward. The outward movement of the plunger 1724 is limited by the abutment of the distally directed face of the plunger head 1726 against cap end plate 410.

Inner coupler 1740, as seen best in FIG. 47, is formed with a number of legs 1742, only one identified, that are arranged in a circle. Legs 1742 are substantially identical in shape and function to legs 458 of previously described inner coupler 450. The legs 1742 extend to a cylindrical head 1744. Head 1744 has an outer diameter greater than the outer diameter of the circle defined by legs 1742.

The inner coupler 1740 is formed with two bores that are centered on the longitudinal axis through the coupler 1740. A first one of the bores, bore 1748, extends distally forward from the distal end of the void space defined by the circle of legs 1742. The internal wall of the coupler 1740 that defines bore 1748 is formed with threading (not identified). A bore 1750 extends from the distal end of bore 1748 to the distally directed face of coupler head 1744. Bore 1750 is smaller in diameter than bore 1750.

Figure 46:
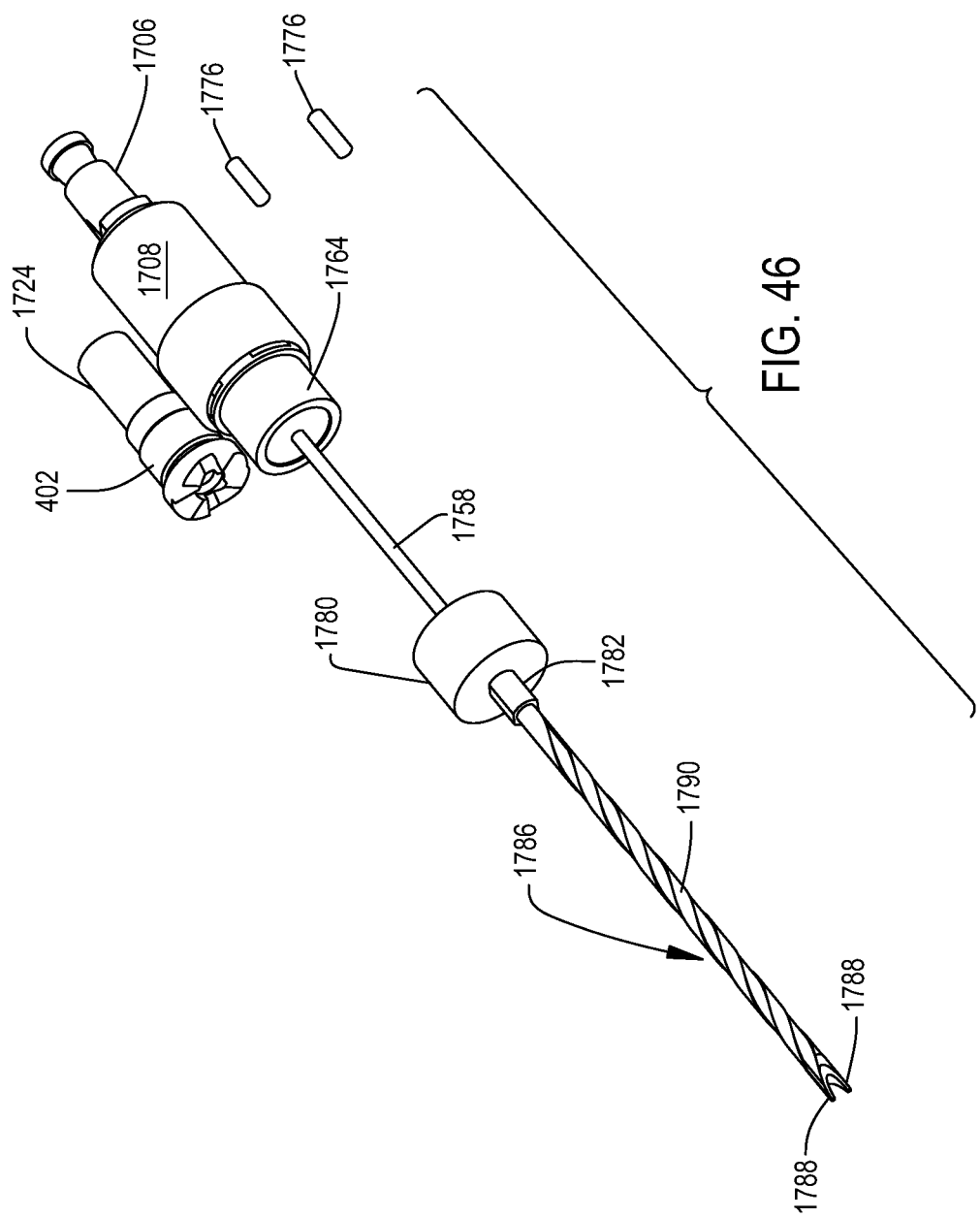
FIG. 46 is a second exploded view of the surgical drill of FIG. 43.

Inner drill bit 1754, as seen in FIG. 46, is press fit in coupler bore 1750 and extends distally forward from the coupler 1740. Drill bit 1754 includes an elongated shaft 1756. The bit 1754 is formed with cutting flutes 1758 at the distal end of the shaft 1756.

Plunger stem distal section 1730 is threaded to the threading that surround inner coupler bore 1748. It should thus be appreciated that the plunger 1724, the inner coupler 1740 and the inner drill bit 1754 moves as a single piece unit.

The outer coupler 1762 is disposed in the input drive shaft head 1710 so as to be between the head 1710 and the inner coupler 1740. The outer coupler 1762, as seen best in FIGS. 45 and 49, includes a shell 1764 that is generally tube like in shape. More particularly, coupler shell 1764 is designed so that the inner coupler 1740 can fit and rotate within the shell. Shell 1764 is further dimensioned so the shell can fit within bore 1720 internal to the input drive shaft 1704. In terms of length, both the inner coupler 1740 and outer coupler 1762 are designed so as to be seat in the input drive shaft bore 1720 and project forward from the input drive shaft 1704.

Coupler shell 1764 is further formed to have slightly forward of the proximal end of the shell a ring 1766 that protrudes outwardly from the portions of the shell proximal and distal to the ring. Ring 1766 is formed to have four indentations 1768, only two seen in FIG. 45. Indentations 1768 have the same surfaces and are essentially identical to indentations 612 of outer coupler 600 (FIG. 31).

At the proximal end of shell 1764, the outer coupler 1762 is further formed to have four arcuately shaped ribs 1770, (one identified). Ribs 1770 are essentially identical to and have the surfaces of ribs 572 integral with retaining cap 550 (FIGS. 25-28). Ribs 1772 project inwardly from the shell 1764 to project over the proximal end of the through bore that extends through the shell. When surgical drill 1700 is assembled, the plunger proximal stem proximal section 1728 extends through the center opening between the ribs 1772. Legs 1742 integral with the inner coupler 1740 extend through the arcuately spaced apart slots between the adjacent ribs 1772. These slots are understood to be analogues to retaining cap slots 572 (FIGS. 26 and 28).

Pins 1776, two seen in FIG. 46, are seated in outer coupler indentations 1768. Pins 1776 perform the same function as previously described pins 902 (FIG. 37).

Figure 49:
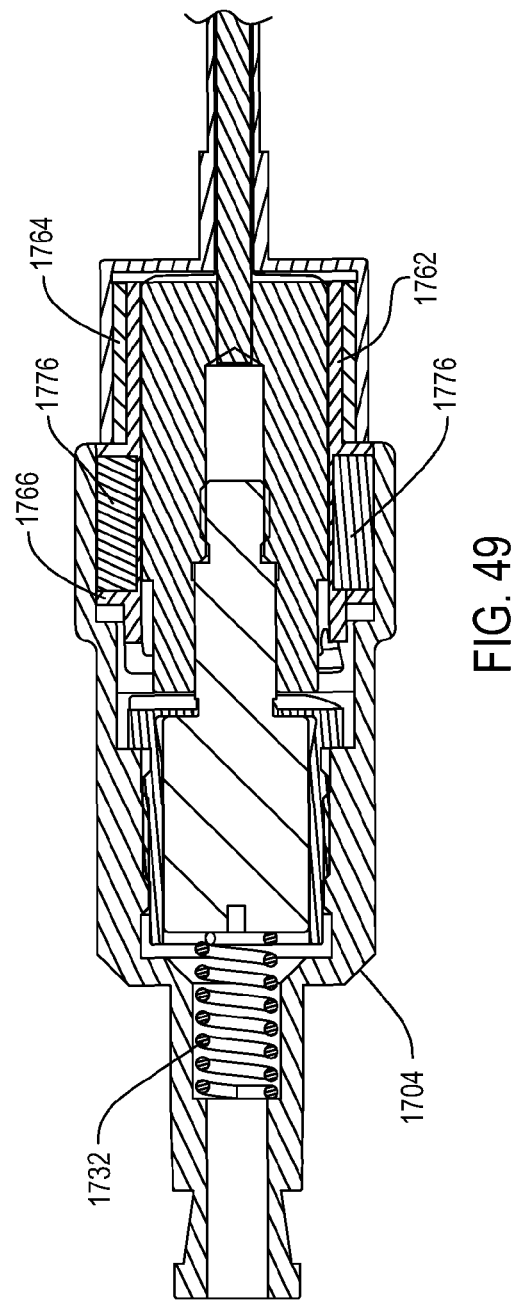
FIG. 49 is a cross sectional view of the inner coupler and inner drill bit of the surgical drill of FIG. 43.

A cap 1780, seen best in FIGS. 46 and 49, is fitted over the portion of the coupler shell 1764 that extends forward of the input drive shaft head 1710. Cap 1780 may be fitted to the outer coupler 1762 by press fitting, threading, adhesive, welding or any means to ensure that the cap rotates in unison with the outer coupler. A tube like nose 1782 extends distally forward from the center of the cap 1780

Outer drill bit 1786, seen in FIGS. 43 and 46 is a sleeve like structure. The proximal end of the drill bit 1786 is press fit in nose 1782 integral with cap 1780. Two cutting teeth 1788, similar to cutting flutes 258 of drill bit 250 (FIG. 4) extend forward from the distal end of the bit. Two flutes 1790 extend helically along the outer surface of the drill bit 1786.

Drill assembly 1700 is used in the same basic manner in which drill 100 is used. Spring 1732 normally urges plunger 1724 so as to result in the legs 1742 of the inner coupler 1740 being held out of engagement with the drive cap 402. When the drill assembly 1700 is pressed against unyielding force, the bone to be cut, sufficient manual force is exerted to overcome the force of spring 1732. Plunger 1724 and inner coupler 1740 are urged proximally. As a consequence of this movement the inner coupler legs 1742 seat in the drive cap notches 414.

The forward rotation of the handpiece chuck to which the input drive shaft 1704 is attached results in a like rotation of the shaft. This rotational movement is transferred to the inner coupler 1740 by the abutment of the drive cap walls 418 against the adjacent surfaces of the inner coupler legs 1742. Inner drill bit 1754 is thus driven into forward rotation. The inner coupler legs 1742 press against the ribs 1770 of the outer coupler 1762. This results in a like forward rotation of the outer coupler 1762. The movement of the outer coupler 1762 causes a like simultaneous rotation of the outer drill bit 1786.

As long as the inner drill bit 1754 is subjected to appreciable front loading (resistance) coupler legs 1742 remain seated in drive cap notches 418. When the bit 1754 is no longer exposed to this resistance, spring 1732 exerts sufficient force to urge the plunger 1724 and associated components forward. Inner coupler legs 1742 are forced out of the drive cap notches 414. The drill bits 1754 and 1786 are stopped rotation as previously described with respect to bits 202 and 250.

Reverse rotation of the input drive shaft 1704 results in pins 1776 undergoing the movement within outer coupler indentations 1768 that pins 902 undergo in indentations 612. The pins become wedged between the input drive shaft 1702 and the outer coupler 1762. This results in the rotation of the outer coupler 1762 and the outer drill bit 1786. The movement of the outer coupler 1762 forces the inner coupler 1740 and attached inner drill bit 1754 into a like reverse rotation.

A benefit of the surgical drill assembly 1700 of this embodiment of the invention is the need to provide a chuck assembly for holding the inner and outer bits 1754 and 1786 to the rest of the assembly is eliminated.

VIII. Alternative Versions

The surgical drill of this invention may have constructions different from what has been described above. The components of the described embodiments of the invention may be combined.

Likewise there is no requirement that in all versions of the inventions, each of the above, described features be present. For example, the 270-in-slot 266 is provided for convenience in some drill bit assemblies. Other versions of the invention may not have these components. This eliminates the need to mount the bit assembly to ensure that the inner bit drive head 210 is seated to ensure that, the outer bit annular flange 262 is properly orientated so that grooves 268 will be in registration with the pins 694 attached to outer coupler 600.

Similarly, there is no requirement that in all versions of the invention the drill assembly include both an inner and outer drill bits. In some versions of the invention, the drill assembly, instead of having an outer drill bit, only has an outer sleeve that provides the interface between the drill assembly and the outer coupler. Likewise, in some versions of the invention, the outer coupler and inner drill bit are formed with geometric features that facilitate the engagement of the inner drill bit to the outer coupler. In these versions of the invention, it may not be necessary to provide any outer member of the inner drill bit. Thus the drill assembly of this version of the invention is a single one-piece bit.

In an alternative embodiment, a biasing component such as a spring (not shown) is mounted between vertical walls 614 and pins 902 so as to bias pins 902 away from vertical walls 614.

Similarly, alternative clutch mechanisms can be provided to upon, disengagement of the first clutch, only allow rotation of the drill bit when the drill is driven in the first direction. For example, in one such alternative construction of the invention, the outer coupler may be provided with pins or bearings. Biasing members, springs, urge these pins/bearings radially outwardly. The input drive shaft is provided with surfaces against which the pins/bearings seat. More particularly these surfaces have geometries such that the shaft rotates in one direction, the pins/bearings slip over the surfaces. When the input drive shaft rotates in the opposed direction, the reverse direction, the pins/bearings are held fast against these surfaces. The abutment of the pins/bearings with these surfaces transfers the torque output by the input drive shaft to the outer coupler.

Likewise there is no requirement that, in all versions of the invention, the chuck be separate from the handpiece. Thus, in alternative versions of the invention, the clutch may be integral with the handpiece 102. Likewise, the illustrated features of the chuck 300 that facilitate the coupling of the chuck to the handpiece 102 are understood to be exemplary, not limiting. Alternative chucks of this invention may include other features that cooperate with locking members integral with the handpiece to facilitate the releasable attachment of the chuck to the handpiece.

Not all components may be present in all versions of the invention. For example, the pin 270-in-slot 266 is provided for convenience in some drill bit assemblies. Other versions of the invention may not have these components. This eliminates the need to mount the bit assembly to ensure that the inner bit drive head 210 is seated to ensure that, the outer bit annular flange 262 is properly orientated so that grooves 268 will be in registration with the pins 694 attached to outer coupler 600.

Likewise, in some versions of the invention, only when the drum or other clutch component that moves linearly, moves to the disengaged state with regard to the input drive shaft does this component move into engagement with the second clutch assembly that applies the reverse rotational moment to the drill bit.

Further there is no requirement that in all versions of the invention, the clutch that applies forward rotational moment to the drill bit be a linear type clutch. Similarly, there is no requirement that in all versions of the invention the clutch that applies reverse rotational moment to the drill bit be a rotary type clutch.

The invention is not limited to chucks designed so that a combination of ramp movement and spring force cause the inner coupler 450 to disengage from the input drive shaft. In some versions of the invention, the translational of the rotational movement into axial movement by the abutting ramps may be all that is necessary to cause the inner coupler to disengage from the input drive shaft 700. In these versions of the invention, the spring or other biasing member may or may not be provided. Often the biasing member is provided to prevent the rattling of the inner coupler 450 against the drive cap 402. Still in other versions of the invention the force of the spring or other biasing member alone is sufficient to, when the drill bit assembly is no longer subjected to axially loading, displace the inner coupler 450 to the disengaged state.

Similarly, there is no requirement that in all versions of the invention the drill assembly include both an inner and outer drill bits. In some versions of the invention, the drill assembly, instead of having an outer drill bit, only has an outer sleeve that provides the interface between the drill assembly and the outer coupler. Likewise, in some versions of the invention, the outer coupler and inner drill bit are formed with geometric features that facilitate the engagement of the inner drill bit to the outer coupler. In these versions of the invention, it may not be necessary to provide any outer member of the inner drill bit. Thus the drill assembly of this version of the invention is a single one-piece bit.

Other assemblies may be used to hold the drill bit to the chuck. These assemblies include arrangements wherein a moveably pin is selected seated or withdrawn from a proximal end slot integral with the outer drill bit. Sometimes this slot is molded into a hub integral with the drill bit. Still other assemblies for removably holding the drill bit include collets with legs that are selectively pressed against the drill bit feet they are used to hold to the chuck.

It should be understood that in other versions of the invention, the handpiece need not be battery powered.

It is therefore the object of the appended claims to cover all such modifications and variations that come within the true spirit and scope of this invention.

What is claimed is:

1. A surgical drill, said drill said drill including:
an input drive shaft configured to receive the rotational output of a handpiece;
a first clutch having: a first clutch input member connected to said input drive shaft to rotate with said input drive shaft; a first clutch output member configured to selectively engage with or disengage from said first clutch input member wherein, when said first clutch output member is engaged with said first clutch input member, said first clutch output member rotates with said first clutch input member and, when said first clutch output member is disengaged from said first clutch input member, said first clutch output member does not rotate with said first clutch input member; and a biasing member that, in the absence of an opposite force, places a force on said first clutch output member to hold said output member in a disengaged state relative to said first clutch input member;
a second clutch having: a second clutch input member that is connected to said input drive shaft to rotate with said input drive shaft; a second clutch output member that is separate from said second clutch input member; a coupling assembly that extends between said second clutch input member and said second clutch output member for: when said second clutch input member rotates in a first direction, causing said second clutch output member to rotate with said second clutch input member; and when said second clutch input member rotates in a second direction opposite the first direction, does not cause second clutch output member to rotate with said second clutch input member; and
at least one drill bit configured to perform a medical procedure on tissue, said at least one drill bit being connected to said first clutch output member and to said second clutch output member to rotate with said output members and to place a force on said first clutch output member opposition to the force placed on said first clutch output member by said first clutch biasing member.

2. The surgical drill of claim 1 wherein said first clutch input member and said second clutch input member are collectively a unitary structure.

3. The surgical drill of claim 1, wherein said first clutch is constructed so that said first clutch output member is configured so that said first clutch output member moves towards and away from said first clutch input member.

4. The surgical drill of claim 1, wherein said second clutch input member is disposed over said second clutch output member.

5. The surgical drill of claim 1, further including a coupling assembly that removably holds said at least one drill bit to said first clutch output member and said second clutch output member.

6. The surgical drill of claim 1, wherein:
there are inner and outer said drill bits that are separate from each other, said outer drill bit being disposed over said inner drill bit and said inner and outer drill bits are connected together to rotate in unison; and
one of said inner drill bit or said outer drill bit is connected said first clutch output member to rotate with said first clutch output member and the other of said outer drill bit or said inner drill bit is connected to said second clutch output member to rotate with said second clutch output member.

7. The surgical drill of claim 1, wherein:
said input drive shaft is formed with a bore; and
at least one of said first clutch output member or said second clutch output member is moveably disposed in the bore of said input drive shaft.

8. A surgical drill, said drill said drill including:
an input drive shaft configured to receive the rotational output of a handpiece;
a first clutch having: a first clutch input member connected to said input drive shaft to rotate with said input drive shaft; a first clutch output member configured to selectively engage with or disengage from said first clutch input member wherein, when said input drive shaft rotates in a first direction and an axial load is placed on said first clutch output member, said first clutch output member engages with said first clutch input member so as to rotate with said first clutch input member and, upon the removal of the axial load on said first clutch output member, said first clutch output member disengages from said first clutch input member so as to stop rotating; and
a second clutch having: a second clutch input member that is connected to said input drive shaft to rotate with said input drive shaft; a second clutch output member that is separate from said second clutch input member; and a coupling assembly that extends between said second clutch input member and said second clutch output member for: when said second clutch input member rotates in the first direction, disconnecting said second clutch output member from said second clutch input member so that said second clutch output member does not rotate with said second clutch input member; and when said second clutch input member rotates in a second direction opposite the first direction, connecting said second clutch input member to said second clutch output member so that said second clutch output member rotates with said second clutch input member; and
a chuck configured to removably hold a drill bit that is configured to be applied to tissue in order to perform a medical procedure, said chuck connected to said first clutch output member and to said second clutch output member to rotate with said output members and to removably place an axial load received from said drill bit on said first clutch output member.

9. The surgical drill of claim 8, wherein:
said input drive shaft is formed with a bore; and
at least one of said first clutch output member or said second clutch output member is moveably disposed in the bore of said input drive shaft.

10. The surgical drill of claim 8, wherein said input drive shaft is formed with features to facilitate the releasably coupling of said input drive shaft to the handpiece that rotates said input drive shaft.

11. The surgical drill of claim 8, further including a biasing member that, in the absence of an axial load being placed on said first clutch output member, holds said first clutch output member in a disengaged state.

12. The surgical drill of claim 8, wherein said second clutch includes at least one pin that is capable of movement relative to said second clutch output member such that: when said at least one pin is in a first position relative to said second clutch output member, said pin does not transfer the rotation of said second clutch input member to said second clutch output member; and when said at least one pin is a second position relative to said second clutch output member that is different from the first position, said pin transfers the rotation of said second clutch input member to the second clutch input member.

13. The surgical drill of claim 12, wherein said second clutch has a plurality of said pins.

14. The surgical drill of claim 12, wherein said at least one pin of said second clutch is capable of movement within said second clutch so that when said second clutch input member rotates in the first direction, said at least one pin engages in rotational movement around an axis of said pin.

15. The surgical drill of claim 8, wherein said input drive shaft, said first clutch input member and said second clutch input member are connected together to rotate as a unitary structure.

16. The surgical drill of claim 8, wherein said first clutch is constructed so that said first clutch output member is configured so that said first clutch output member moves towards and away from said first clutch input member.

17. The surgical drill of claim 8, wherein said second clutch input member is disposed over said second clutch output member.

18. The surgical drill of claim 8, wherein:
said input drive shaft is formed with a bore; and
said first clutch output member and said second clutch output member are moveably disposed in the bore of said input drive shaft.

19. The surgical drill of claim 8, wherein said chuck is configured to releasably hold inner and outer drill bits that are separate from each other to said first and second clutches wherein, when the drill bits are so secured, the outer drill bit is disposed over said inner drill bit and said chuck connects one of said inner drill bit or said outer drill bit to said first clutch output member to rotate with said first clutch output member and the other of said outer drill bit or said inner drill bit to said second clutch output member to rotate with said second clutch output member.

20. The surgical drill of Claim 8, wherein said chuck is configured to releasably hold inner and outer drill bits that are separate from each other to said first and second clutches wherein, when the drill bits are so secured, the outer drill bit is disposed over said inner drill bit and said chuck connects the inner drill bit to said first clutch output member to rotate with said first clutch output member and the outer drill bit to said second clutch output member to rotate with said second clutch output member.

* * * * *